US006436056B1

(12) United States Patent
Wang et al.

(10) Patent No.: US 6,436,056 B1
(45) Date of Patent: Aug. 20, 2002

(54) POLYMERIC IMPLEMENTS FOR TORQUE TRANSMISSION

(75) Inventors: James C. Wang, Norton; Albert Chin, Newton, both of MA (US); James B. Daigle, Morgan Hill, CA (US); Douglas J. Daniels, Mendon, MA (US); Richard M. Demello, Acton, MA (US); John F. Hartnett, Wellesley, MA (US); Robert E. Reid, Westborough, MA (US); Christopher A. Rowland, Marlborough, MA (US); Charles Warich, Milford, MA (US); Thomas A. Svatek, Carlisle, MA (US)

(73) Assignee: Boston Scientific Corporation, Natick, MA (US)

( * ) Notice: Subject to any disclaimer, the term of this patent is extended or adjusted under 35 U.S.C. 154(b) by 0 days.

(21) Appl. No.: 09/114,458

(22) Filed: Jul. 13, 1998

Related U.S. Application Data

(62) Division of application No. 08/784,417, filed on Jan. 16, 1997, now Pat. No. 5,951,494, which is a continuation of application No. PCT/US96/02265, filed on Feb. 28, 1996.

(51) Int. Cl.[7] ............................................... A61B 5/00
(52) U.S. Cl. ...................................................... 600/585
(58) Field of Search ................................ 600/434, 435, 600/585; 264/339

(56) References Cited

U.S. PATENT DOCUMENTS

| | | | |
|---|---|---|---|
| 4,257,421 A | 3/1981 | Beal | |
| 4,627,472 A | 12/1986 | Goettler et al. | |
| 4,704,886 A | * 11/1987 | Evert et al. | 72/57 |
| 4,724,846 A | 2/1988 | Evans, III | |
| 4,737,715 A | 4/1988 | Shimamura et al. | |
| 4,764,324 A | 8/1988 | Burnham | |
| 4,790,831 A | 12/1988 | Skribiski | |
| 4,867,174 A | 9/1989 | Skribiski | |
| 4,874,376 A | 10/1989 | Hawkins, Jr. | |
| 4,932,419 A | 6/1990 | de Toledo | |
| 4,963,306 A | * 10/1990 | Weldon | 264/101 |
| 5,024,617 A | 6/1991 | Karpiel | |
| 5,054,501 A | 10/1991 | Chuttani et al. | |
| 5,069,226 A | 12/1991 | Yamauchi et al. | |
| 5,095,915 A | 3/1992 | Engelson | |
| 5,133,364 A | 7/1992 | Palermo et al. | |
| 5,156,785 A | 10/1992 | Zdrahala | |
| 5,228,453 A | 7/1993 | Sepetka | |
| 5,248,305 A | 9/1993 | Zdrahala | |
| 5,271,415 A | 12/1993 | Foerster et al. | |
| 5,275,173 A | 1/1994 | Samson et al. | |
| 5,292,320 A | 3/1994 | Brown et al. | |
| 5,299,580 A | 4/1994 | Atkinson et al. | |
| 5,326,524 A | * 7/1994 | Rhodes et al. | 264/294 |
| 5,333,620 A | 8/1994 | Moutafis et al. | |
| 5,377,690 A | 1/1995 | Berthiaume | 128/772 |
| 5,385,152 A | 1/1995 | Abele et al. | 128/772 |
| 5,405,338 A | 4/1995 | Kranys | |
| 5,711,909 A | * 1/1998 | Gore et al. | 264/320 |

* cited by examiner

*Primary Examiner*—Max Hindenburg
(74) *Attorney, Agent, or Firm*—Fish & Richardson P.C.

(57) ABSTRACT

Implements, particularly medical instruments, formed at least in part of elongated polymer members, exhibit high torque fidelity after processing with tension, heat, and twisting. The processing orients the polymer in generally helical paths so that torque imposed at the proximal end can be transmitted to the distal end without substantial whipping, even if the implement follows a long and tortuous pathway. Applications include medical guidewires, catheters, and driveshafts.

51 Claims, 18 Drawing Sheets

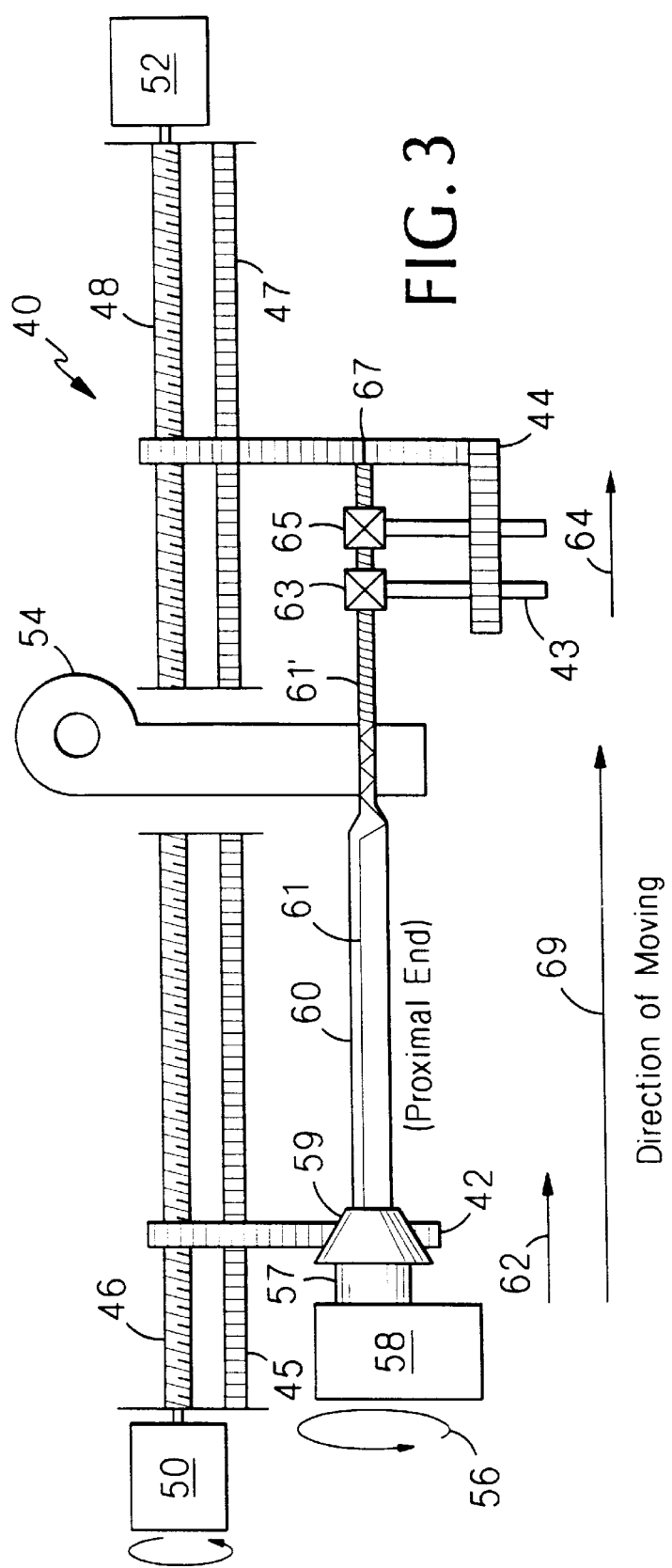
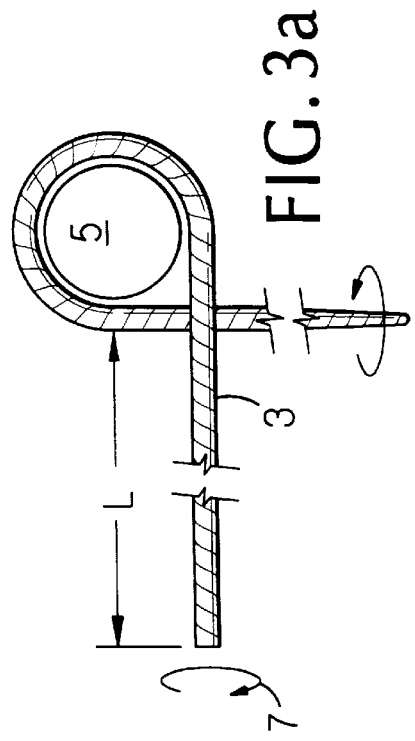
FIG. 3
FIG. 3a

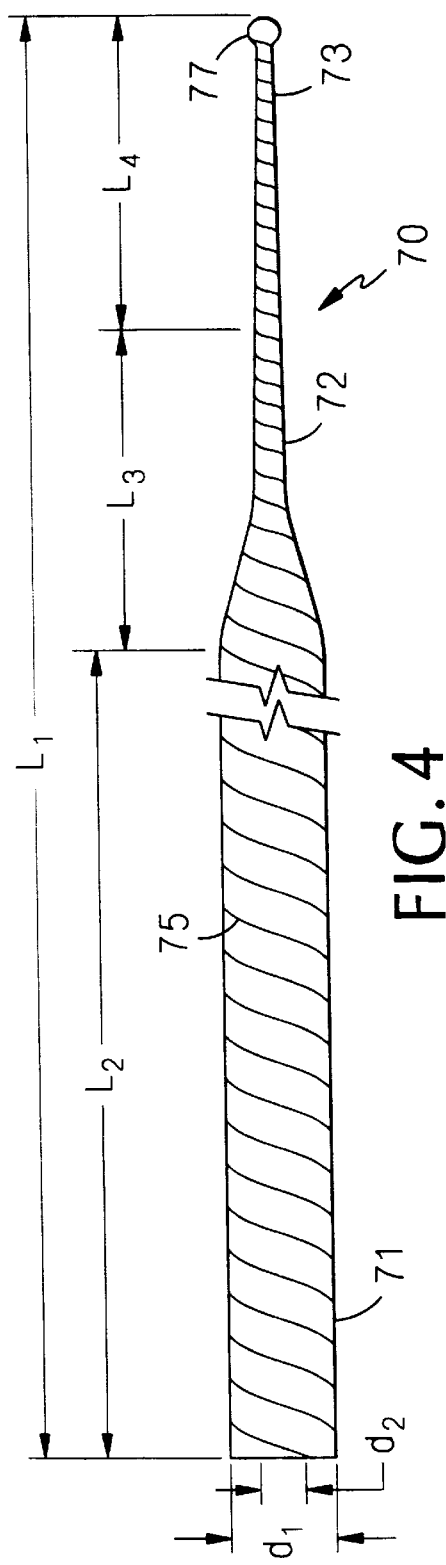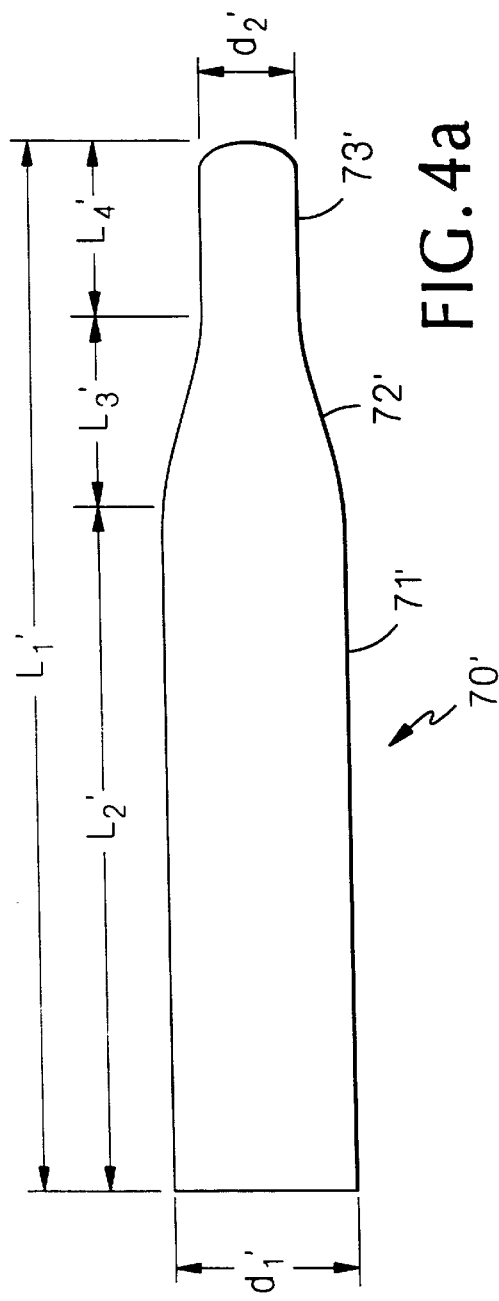
FIG. 4
FIG. 4a

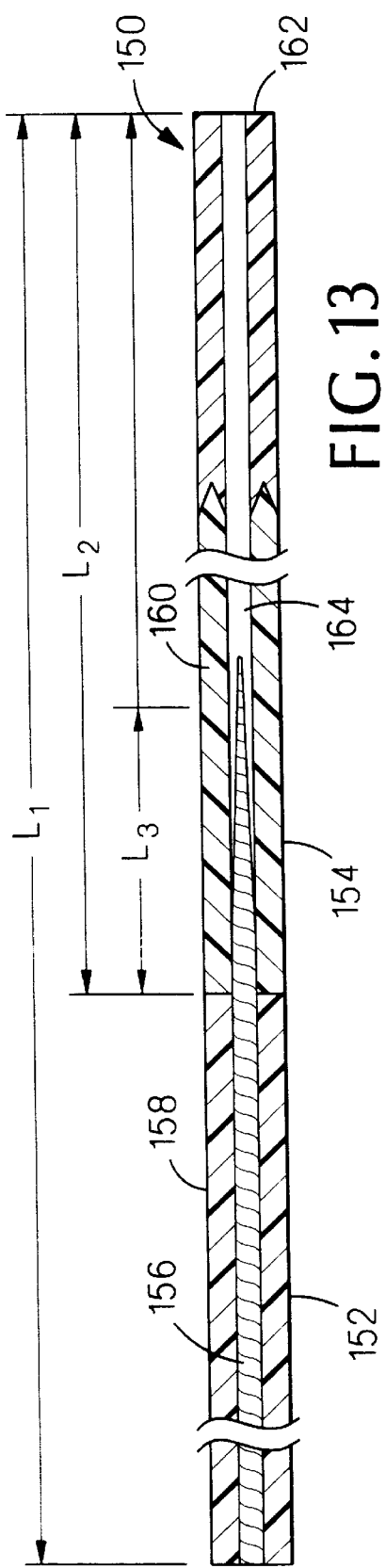
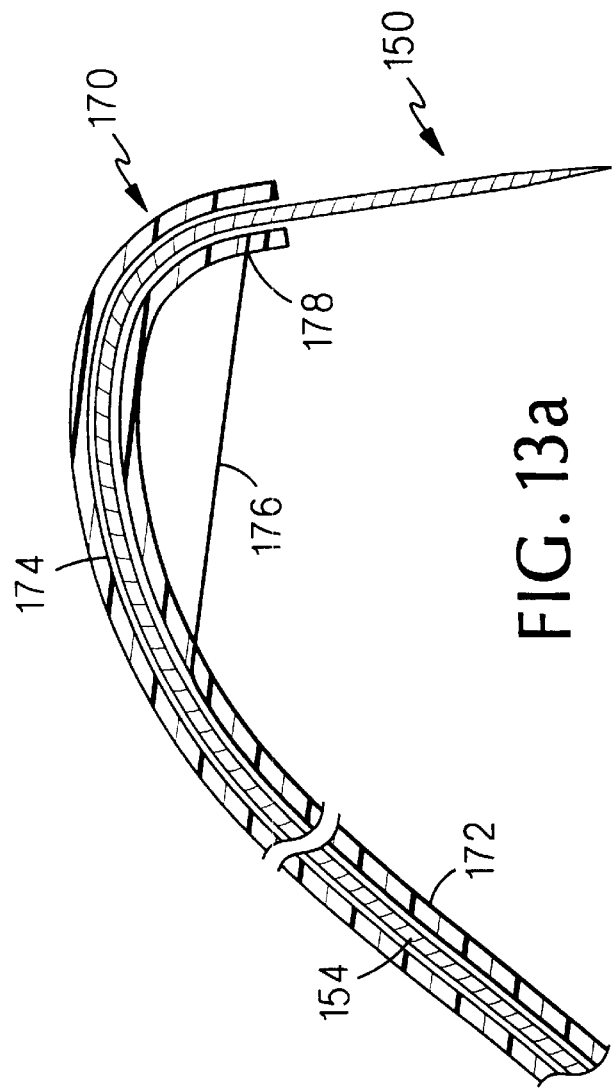
FIG. 13
FIG. 13a

POLYMERIC IMPLEMENTS FOR TORQUE TRANSMISSION

CROSS REFERENCE TO RELATED APPLICATIONS

Under 35 USC §120, this is a divisional application which claims the benefit of prior U.S. application Ser. No. 08/784,417, filed Jan. 16, 1997, now U.S. Pat. No. 5,951,494 which is a continuation of PCT/US02265, filed Feb. 28, 1996.

FIELD OF THE INVENTION

This invention relates to polymeric implements that transmit torque.

BACKGROUND OF THE INVENTION

Torque transmission is important in many areas. For example, in the field of less invasive surgery, catheters and guidewires are threaded along tortuous paths to treatment sites deep within the body by torquing and pushing their proximal end. Positioning these devices is easier if they have torque transmission characteristics such that when the physician rotates the proximal end, the distal end rotates by a corresponding amount. Accurate torque transmission is also important for medical devices with rotating parts, such as an acoustic imaging catheter with a transducer that is rotated by a driveshaft.

SUMMARY OF THE INVENTION

In an aspect, the invention features an elongated medical instrument formed at least in part by an extended element that is subject to torque in use. The element is a structural body composed of polymer that is helically oriented about the instrument axis.

In another aspect, the invention features an elongated medical instrument formed at least in part of an extended element that is a structural body composed of polymer. The element has a length between about 40 to 300 inch and an outer diameter of about 0.25 inch or less. The element is capable of substantially 1:1 torque transmission between the proximal and distal ends without substantial whipping when the member is looped in a circle with a diameter about 5 inch at a point about half way along its length.

In another aspect, the invention features an elongated medical instrument formed at least in part of an extended element and a method for forming the element. The element is a structural body that is composed of polymer and which is the product of the process of providing an elongated polymer member, heating the polymer member above its glass transition temperature but below its melting temperature, simultaneously twisting and tensioning member, and cooling the member to set the effect of the twisting and tensioning into the member.

Embodiments may include one or more of the following. The element may have a length of about 40 inch or more and a diameter of about 0.25 to 0.008 inch. The helical paths may have a pitch length that is about 1.5 or more times the outer diameter of the element. The helical paths may have a pitch length from about 2 to about 5 times the outer diameter of the element.

Embodiments may also include one or more of the following. The medical instrument may be composed entirely of polymer. The polymer may be a semi-crystalline polymer. The polymer may be PET, Nylon, or PEBAX. The polymer may be oriented or heat set at a temperature substantially greater than sterilization temperature.

Embodiments may also include one or more of the following. The element may be in the form of a solid polymer rod. The element may be in the form of a tube. The medical instrument may be in the form of a composite of an elongated metal member and the polymeric element. The element may be a coextrusion of polymers. The element may be a coextrusion of different polymers. The instrument may have differential stiffness along its axis. The element may include polymer molecules oriented on helical paths and polymer molecules oriented linearly, along the axis. The element may include polymer molecules oriented on helical paths oriented about the axis in opposite directions. The element may include a first polymer layer with polymer molecules oriented along helical paths extending in one direction about the axis and a second polymer layer with polymer molecules oriented along helical paths extending in the opposite direction about the axis. The medical instrument may be in the form of a medical guidewire. The medical instrument may be in the form of a medical catheter having a lumen therethrough. The medical instrument of may be stiffer in a proximal portion than a distal portion.

Embodiments may also include one or more of the following. The process may include stretching the member by the tensioning. The process may include placing the polymer member in tension and rotating one end of the polymer member while holding the other end rotationally stationary. The process may include simultaneously heating, twisting, and stretching. The process may include providing a member having differential stiffness along its length. The process may include heating to improve dimensional stability. The process may include forming a tube by providing an elongated polymer member constructed of a jacket and core composed of different polymers, heating, twisting, tensioning, and cooling the member, heating to a temperature sufficient to melt or relax the core polymer without melting or relaxing the core polymer, and removing the core polymer to form a lumen.

In another aspect, the invention features an apparatus for manufacturing an elongated element that is subject to torque in use and composed of polymer. The apparatus includes first and second holding stations spaced along a linear path and constructed to grip a preformed polymer member. Translating apparatus is provided for moving the first and second stations along the path to place the preformed polymer member in tension. Torquing device is provided for imposing torque on the preformed member, and a heater is located between the first and second stations for heating a portion of the preformed member.

Embodiments may include one or more of the following. The torquing device may be a rotatable chuck provided at the first holding station. The translating apparatus may be constructed to move the stations along the linear path in the same direction. The translating apparatus may be constructed to move the second station faster than the first station to stretch the member therebetween. The second holding station may include a series of grippers to hold and support a processed length of the member while other portions are processed. The heater may heat the member without contacting the member. The heater may be a heat gun. The translating apparatus may be constructed to vary the translation speed of the stations during the course of processing. The torquing device may be constructed to vary the torque during the course of processing the member. The translating apparatus, torque device, and heater may be constructed to reverse the direction of movement along the path while keeping the member in tension and without torquing, to heat the member to improve dimensional stability. The holding stations and torque device may be constructed to contact the member on its exterior surface. The holding stations and torque device may be constructed to contact a preformed polymer tubular member with a core member extending therethrough in a manner to permit torquing and tensioning the polymer member without torquing or tensioning the core member, while translating the tubular member and core member along the path. The torquing element may be a rotatable chuck positioned at the first station permitting gripping and torquing the polymer member without gripping or torquing the core and the second station includes a gripping element that grips the polymer member and the core together.

In another aspect, the invention features an elongated medical instrument that is delivered into tortuous pathways deep within the body. The instrument has an extended element having differential stiffness along its length, composed of homogenous structural polymer that is helically oriented about the instrument axis.

Embodiments may also include one or more of the following. The element may include polymers of differing stiffness along its length. The element may include variable diameter along its length. The element may be stiffer in proximal portions than distal positions. The instrument may be a tube-form catheter. The instrument may be a solid rod-form. The instrument may be a guidewire.

In another aspect, the invention features an elongated implement that is torqued in use. The implement has an extended element having a first portion composed of a polymer that is helically oriented about the instrument axis and a second portion composed of polymer in a different orientation.

Embodiments may also include one or more of the following. The second portion may be composed of polymer that is helically oriented in the rotational direction opposite the helical orientation of the first portion. The second portion may be composed of polymer that is linearly oriented. The first and second portions may be separate layers. The first and second portions may be disposed along the length of the device. The implement may be in the form of a tube. The implement may be in the form of a solid rod-form. The implement may be in the form of a rotatable drive shaft.

In another aspect, the invention features an elongated implement that is subject to torque in use. The implement includes an extended jacket element composed of polymer that is helically oriented about the implement axis and positioned over a core element.

Embodiments may also include one or more of the following. The core element may be a metal wire. The wire may be a superelastic material. The core may be a glass filament.

In another aspect, the invention features an elongate implement that is subject to torque in use. The implement has a first portion made of an extended jacket element of polymer positioned over a core element, and a second portion composed substantially of a polymer.

Embodiments may include one or more of the following. The core element extends partially into the second portion. The first portion has substantially greater length than the second portion. The second portion is substantially of a polymer that is helically oriented about the instrument axis.

In another aspect the invention features a medical procedure on a body. The procedure includes providing an elongated medical instrument formed at least in part by an extended element that is subject to torque in use. The element is a structural body of polymer that is helically oriented about the instrument axis. The procedure also includes delivering the medical instrument into the body and applying torque to the part comprised of polymer that is helically oriented about the instrument.

Embodiments may also include one or more of the following. The procedure includes providing the medical instrument in the form of a guidewire and delivering the instrument into a body lumen by urging and torquing an end of the instrument. The procedure includes applying electrical or magnetic energy in proximity to the medical instrument. The procedure is a sphincterotomy procedure and the part made of polymer is made entirely of polymer near the distal end of the guidewire. The procedure includes delivering the guidewire into a body lumen, guiding a sphincterotome into the lumen over the guidewire, the sphinctertome including an electrically-energized resecting element near its distal end adapted to resect tissue, and resecting tissue with the resecting element while maintaining the guidewire in axial location corresponding to the resecting element.

Embodiments also include one or more of the following. The medical procedure is performed while simultaneously conducting magnetic resonance imaging of the body. The procedure is a less invasive procedure. The procedure includes delivering a guidewire into the body. The procedure includes delivering a catheter into the body. The procedure includes delivering the medical instrument into the body through an entry needle formed of metal.

Embodiments may also include one or more of the following advantages. For example, whipping can be decreased or eliminated in guidewires, catheters, and other devices. Whipping can occur if torque is not efficiently transmitted, causing a device to become twisted and wound along its length. If the distal end of the member does not respond to the rotational torque applied at the proximal end in a one-to-one relationship, then the torsional energy is stored in the length of the member and the distal tip will whip when a threshold energy is reached.

In embodiments, rotational fidelity between the proximal and distal ends may be substantially 1:1, even for devices of extended length, e.g., 20 inch or more, e.g. 75 inch, that follow a tortuous path, e.g., a tight circle.

Moreover, by providing high torque fidelity components according to the invention, the use of common polymers in medical devices can be extended. Accordingly, the invention can reduce instrument weight, improve device lubricity, simplify manufacture, and lower cost.

Further features, aspects, and advantages follow. For example, in some further aspects, the invention features methods of medical treatment using polymeric torque transmission elements and apparatus for forming polymeric torque transmitting elements, as well as non-medical devices and methods employing torque transmission.

DESCRIPTION OF THE PREFERRED EMBODIMENTS

We first briefly describe the drawings.
Drawings
FIG. 1 is a side view of a polymer medical guidewire, while FIG. 1a is a greatly expanded view of a small portion of a segment of the guidewire that has been oriented to follow a characteristic helical path, and FIG. 1b is a greatly expanded schematic of oriented polymer molecules within the segment;

FIG. 2 is a schematic of the guidewire in FIG. 1 being delivered into a patient, while

FIG. 3 is a top view schematic of an apparatus for manufacture of high torque fidelity instruments, while FIG. 3a is an illustration of a torque transmission test;

FIG. 4 is a cross-sectional side view of a guidewire as described in Example 1, while FIG. 4a is a cross-sectional side view of a member which can be processed to form the guidewire;

FIG. 5 is a cross-sectional side view of a guidewire according to the invention as described in Example 2, while

FIG. 11 is a cross-sectional side view of a catheter as described in Example 6, while

FIG. 12 is a cross-sectional side view of a catheter as described in Example 7, while

FIG. 13 is a cross-sectional sideview of a guidewire described in Example 8, while FIG. 13A is a view of the wire in use with a sphinctertome.

STRUCTURE

Figure 1:
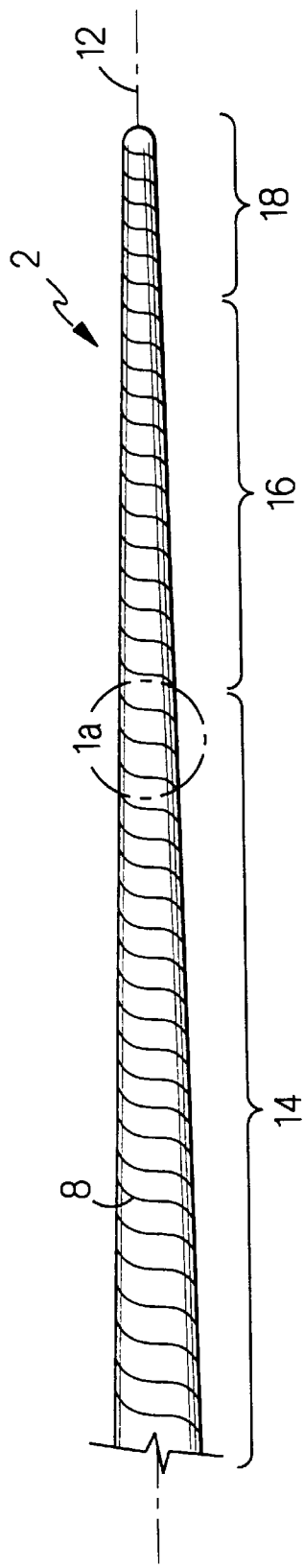

Referring to FIG. 1, a guidewire 2 includes a relatively stiff proximal portion 14, a transition portion 16 with varying, intermediate stiffness, and a highly flexible distal portion 18. The guidewire is formed entirely of common medical polymer materials and exhibits high torque fidelity because it has been twisted and tensioned in manufacture to helically orient the polymer. This is illustrated by a segment 8 of the wire that, prior to processing, was parallel to the device axis but after twisting and tensioning, follows a characteristic helical path.

Figure 1B:
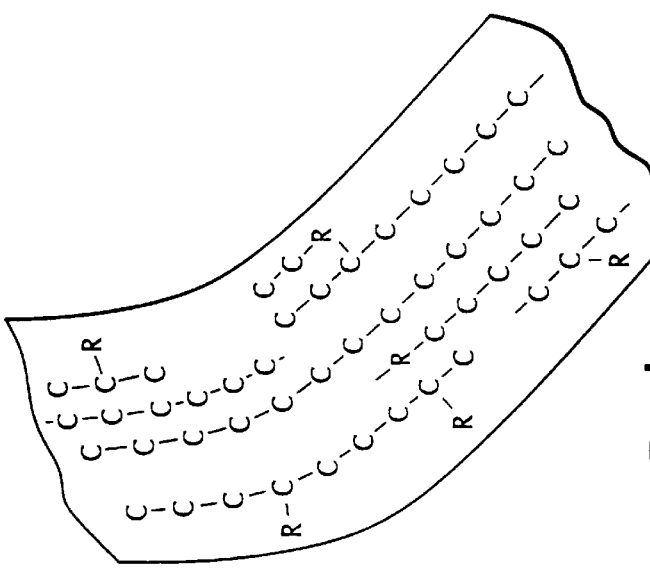
Figure 1A:
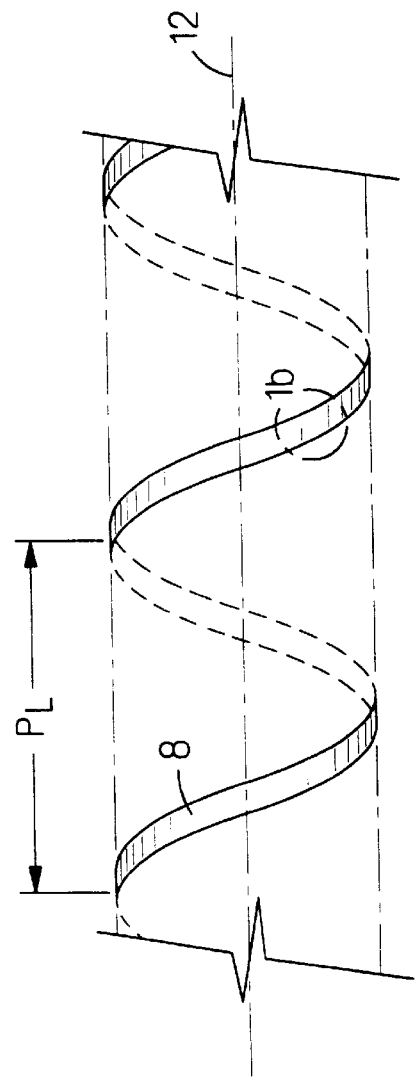

Referring as well to FIG. 1a, a greatly enlarged view of a portion of segment 8, the helical orientation can be characterized by a pitch length PL, which is the length that the characteristic helical path extends along the axis for each 360° rotation about the axis. The pitch length is a measure of how tightly the helical orientation is wrapped about the axis 12. As discussed below, the pitch length can be determined by drawing a line parallel to the axis of a preformed polymer member prior to processing. After processing, the line traces a characteristic helical path which can be measured.

Referring as well to FIG. 1b, a greatly enlarged, molecular level schematic of a portion of the segment 8, it is believed that the molecules of the polymer are oriented along helical paths as a result of twisting and tensioning. This orientation improves the transmission of torque along the length of the guidewire, which can make it easier to deliver through a tortuous body lumen. The process of twisting the polymer, as will be discussed in detail below, reduces asymmetries in the polymer, which reduces or eliminates whipping.

Figure 2:
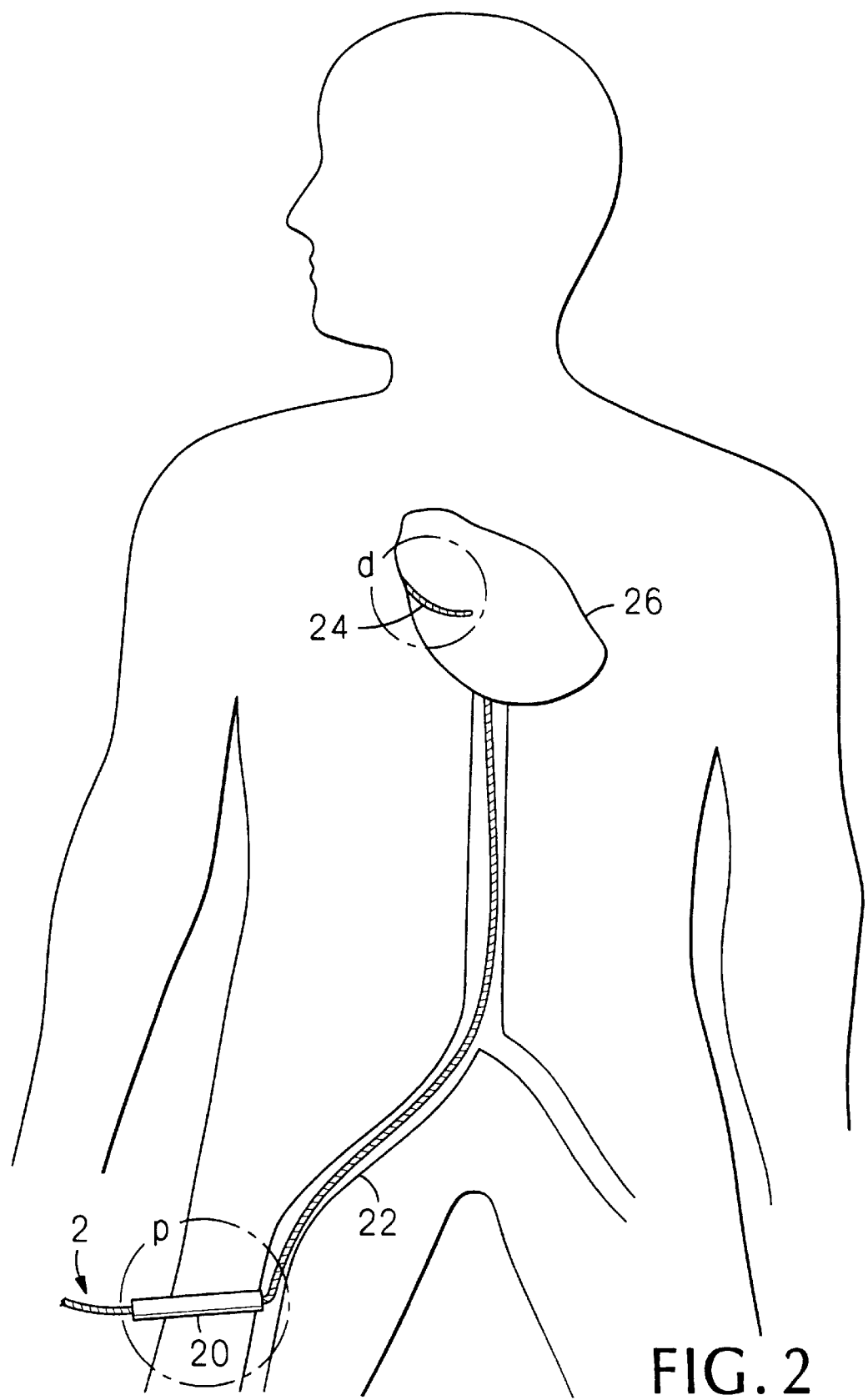

Referring to FIG. 2, in the course of an angioplasty operation to open an occluded coronary artery, the guidewire 2 is typically delivered through an access catheter 20 into the femoral artery 22. The physician pushes and torques the proximal end of the guidewire to thread it through the body into the coronary arteries 24.

Figure 2A:
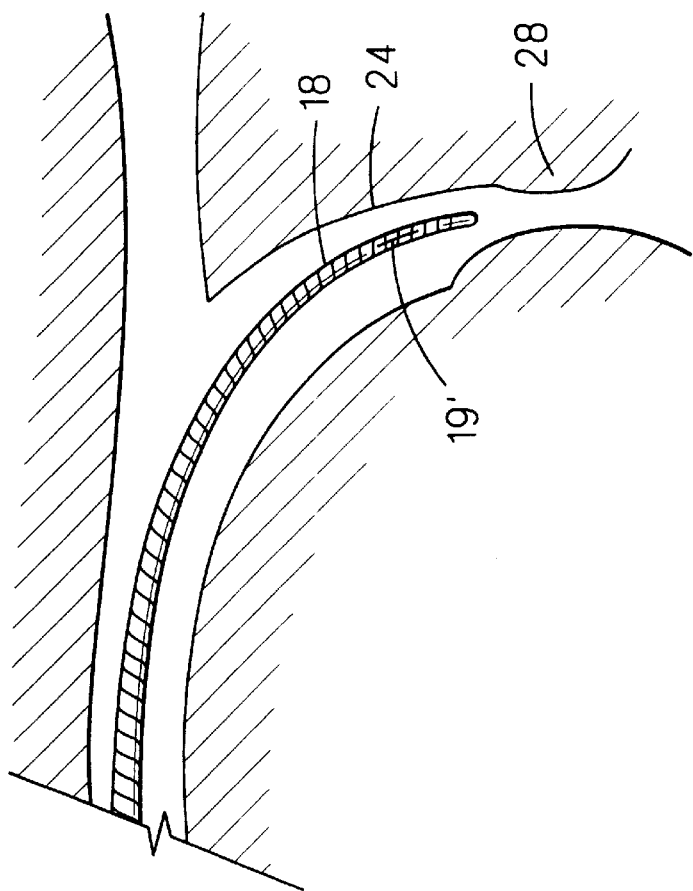
FIGS. 2a and 2b are greatly expanded views illustrating torquing of the proximal end and rotation of the distal end.
Figure 2A:
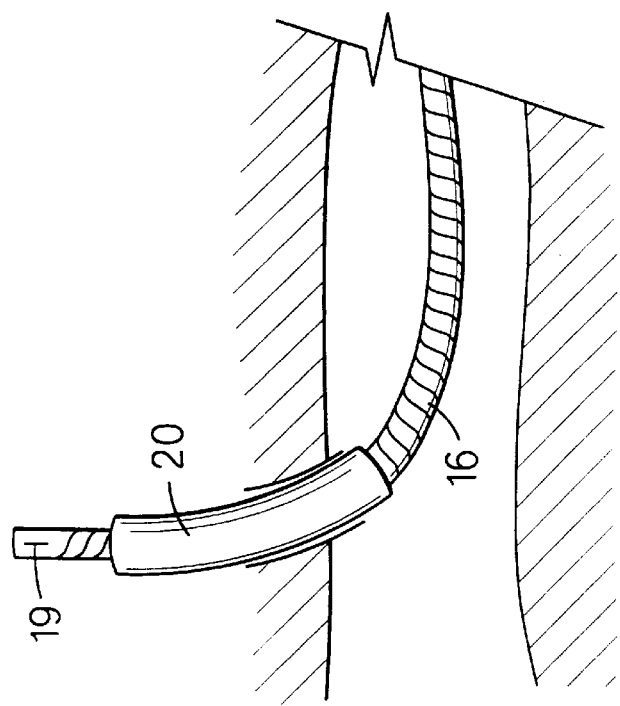
Figure 2B:
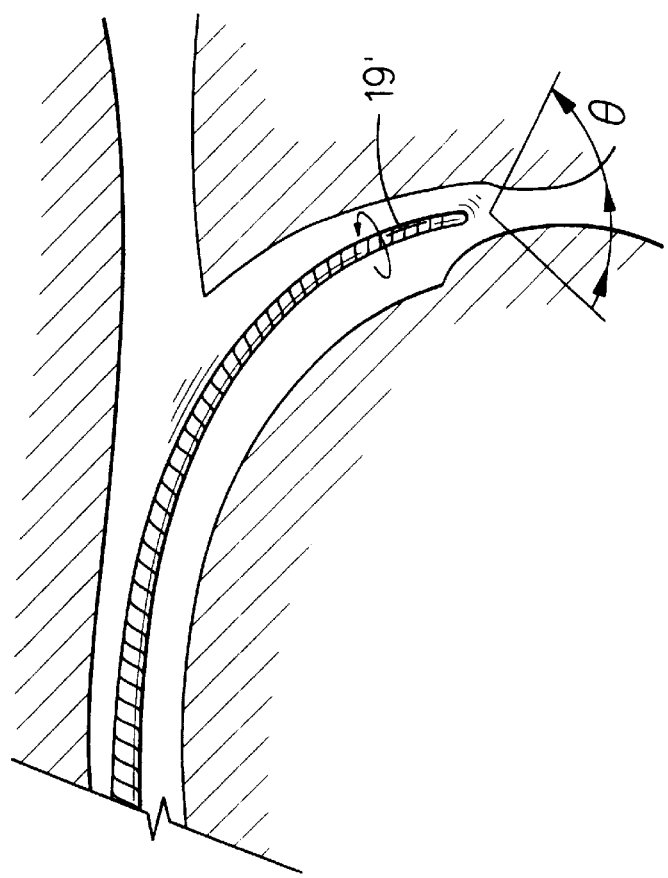
Figure 2B:
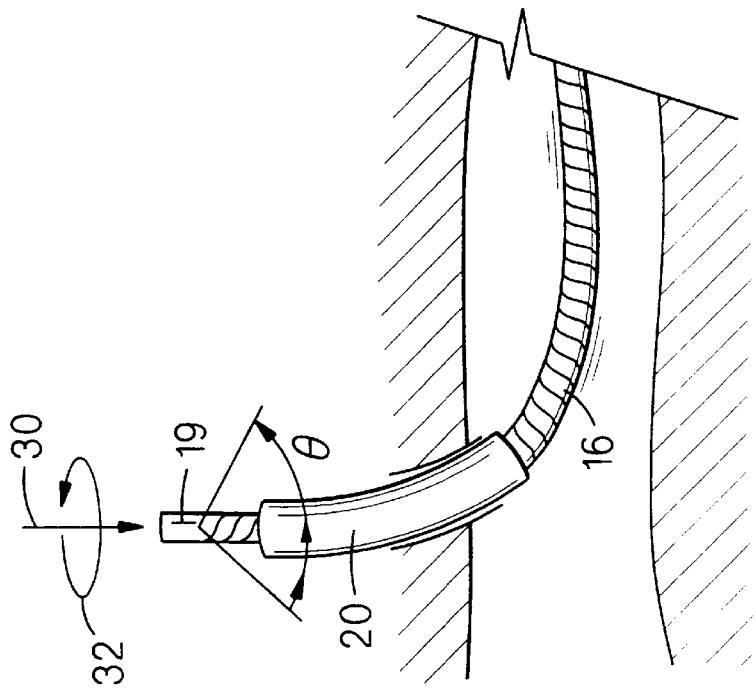

Referring as well to FIGS. 2a and 2b, the distal portion 18 of the guidewire is positioned such that it can cross a restricted region 28 of the artery. The physician pushes (arrow 30) and torques (arrows 32, 33) the proximal portion of the guidewire remaining outside the body. The degree of rotation caused by torquing the proximal end is transmitted to smoothly produce an equal degree of rotation at the distal end. For example, as indicated by marker lines 19, 19' if the physician rotates the proximal end θ, e.g. 60°, the distal end smoothly rotates θ, 60° in the same direction without substantial whipping.

Figure 2C:
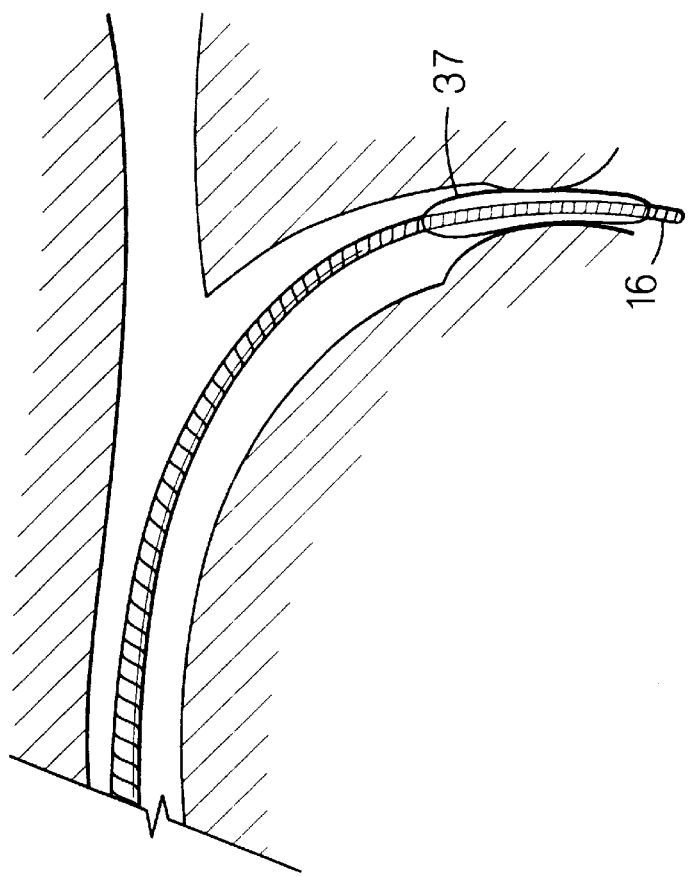
FIG. 2c is a view of an angioplasty catheter being threaded over the guidewire.
Figure 2C:
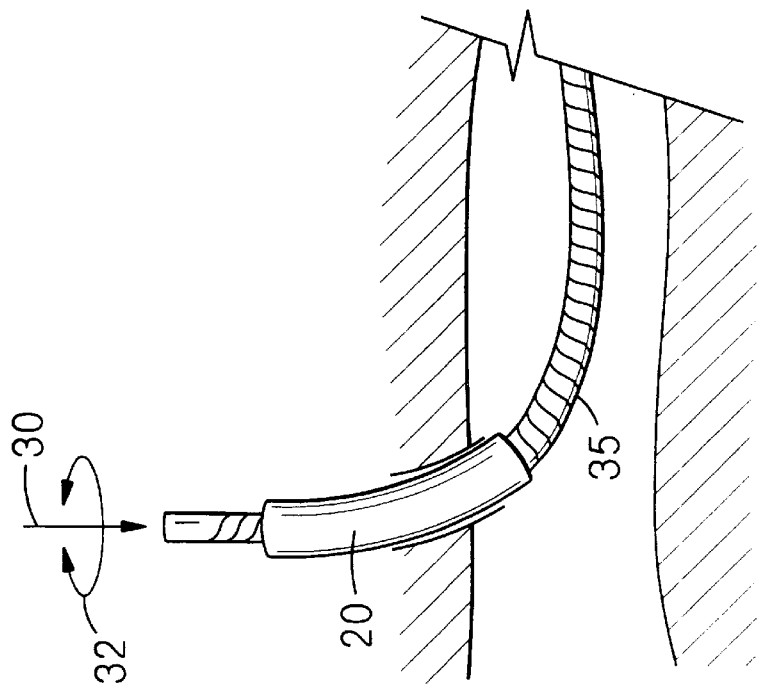

Referring to FIG. 2c, once the guidewire is positioned across the occlusion, a catheter, such as an angioplasty balloon catheter 35 is threaded over the guidewire. The body of the catheter is also formed by twisting to improve its torque transmission to facilitate delivery. The catheter is torqued and pushed from the proximal end to position the balloon 37 adjacent to the occluded area 28. After positioning, the balloon is inflated to expand the restricted area, then deflated, and the catheter and guidewire are removed by torquing and pulling from the proximal end. The guidewire is removed in a similar manner.

Manufacture

Referring to FIG. 3, high torque fidelity devices can be manufactured with a system 40 that permits placing a preformed polymer member 60 in tension, heating the member, stretching the member, twisting the member, and cooling the member. To place the member in tension, the system 40 includes first and second holding stations 42, 44, both of which can be translated along tracks 45, 47 (e.g., 6 foot translation distance) by rotating-screw translators 46, 48 that are driven by motors 50, 52. To twist the member, one end, the proximal end, of polymer member 60 is held at station 42 by a rotatable chuck 59. The chuck is connected to a motor 58 to torque (arrow 56) the member about its axis. The other end of the member is held at station 44 by compression fittings 63, 67, e.g., Touhy-Borst type fittings that do not permit rotation. Fitting 63 and fitting 65 can be positioned at various distances along on arm 43 and set, e.g., with a set screw. The multiple fittings reduce the tension on the distal portion of the member, which is typically thin and soft, while more proximal portions are processed. To heat the member along a short length (e.g., about 1 cm), a heater stage 54 (475 watt heat gun) is provided between the holding stations. Temperature is estimated by measuring the output air of the heat gun with a thermocouple. An infrared heater can also be used.

To improve the torque fidelity of the member 60, the stations 42 and 44 are moved in the same direction but station 44 moves at a higher rate than station 42 (arrows 62, 64), putting the polymer member in tension and causing it to be translated past the heater (arrow 69). At the same time, the end of the member held at station 42 is rotated (arrow 56). The heater 54 directly heats a short section of the member to soften it and permit the member to be stretched due to the tension, while being twisted due to the rotation at station 42. The portions of the polymer that are translated beyond the heater cool and harden, setting the effects of rotation and tension into the polymer.

Referring to FIG. 3, a segment of the preformed member running parallel to the longitudinal axis of the member prior to processing, as indicated by line portion 61, is helically deformed during processing, as indicated by line portion 61'.

The process increases the modulus of the member in the transverse direction. The process also reduces asymmetries (e.g., ridges, troughs, oval, and bends) in the polymer member.

The preformed polymer member may be, for example, in the form of a rod, a tube, polymer-metal composite, or polymer/non-metal composite. Prior to processing, the polymer may have any molecular orientation. For example, the polymer may be completely unoriented or it may be oriented, for example, linearly. The member may be preformed by extrusion, molding or other techniques. The member may be coextruded with multiple polymer layers. The coextrusion may have different polymers along its length that give the member and the finished device variable stiffness. Suitable coextrusion techniques are described in Wang U.S. Ser. Nos. 08/230,333, and 08/230,310, both filed Apr. 20, 1994, their entire contents being incorporated herein by reference. The length and diameter of the preformed polymer member are selected based on the desired length and diameter of the desired oriented device, accounting for the process draw ratio. The length of the member should include some excess to allow for the portion of the member gripped at the holding stations and the length of the heating area. This excess, which is not oriented, is trimmed after processing. For example, in a typical case, approximately 2" is trimmed from the distal end and approximately 10" (mostly not oriented) is trimmed from the proximal end. (Trimming lengths depends on system configuration and dimension and on how far the orientation is allowed to go beyond the needed length.)

The polymer may be a conventional, homogenous, biocompatible structural polymers, such as engineering thermoplastics, with mechanical characteristics, such as flexibility and softness, that are selected based on the desired device performance. For example, the polymer may be a semi-crystalline polymer such as PET or nylon. Non-crystalline or amorphous polymers, such as polyurethanes, may also be worked as described above to improve torque transmission. Since these latter polymer types generally are not heat set, they are used in applications where the temperature is well below the softening or melting temperature, above which the effect of twisting might be relaxed. For most applications, the polymer should be capable of maintaining good torque transmission after being heated to temperatures commonly used for sterilization, such as about 70° C. (e.g., for ethylene oxide sterilization). The polymers that can be used include, for example, polyamides, including nylon 6, nylon 66, nylon 11, nylon 12, Pebax nylons (polyether block amide copolymers, e.g. PEBAX 3533, 5533, 6333, 7033, 6033, 5033), and polyamide elastomers, polyesters including PET (polyethylene terphthalate), PBT (polybutylene terephthalate), PEN, PMMA (polymethyl methacrylate (acrylic)) and polyester elastomers, polyolefins such as polyethylene, polypropylene and polyolefin copolymers and elastomers, polystyrene and its copolymers, including ABS and SAN, polyurethanes including stiff and elastomeric formulations, PVC (polyvinyl chloride) and its copolymers, PVDC (polyvinyl dichloride (Kynar)) EVOH and its copolymers, polycarbonates, and various blends and polymer alloys.

Irradiated polymers can be used as the shaft stock. In this case, a tubing or rod is made from a plastic such as HDPE (high density polyethylene), PVC or other irradiatable polymer is exposed to high-energy electrons in a commercial e-beam vault. The high-energy electrons induce the macromolecules to crosslink and form a three-dimensional network. The crosslinking occurs in the amorphorous regions in semi-crystalline materials such as HDPE. When heated above the original melt temperature and subjected to helical strains in the processing steps, the crystalline regions (which are not crosslinked) will melt while the crosslinked amorphorous regions will deform similar to a natural rubber. When cooled, the crystalline regions reform and "freeze" the amorphorous, crosslinked regions under strain. The application temperatures for an element made with irradiated polymers should not exceed the temperatures used in the helical/longitudinal orientation process to avoid shrinkage of the shafts.

Longer polymer chain lengths may be preferable because, it is believed, they add strength to the device. For devices that will be flexed in use, fibrillation-resistant polymers should be used. Specific polymers can be chosen based on their Young's modulus, durometer, tensile strength, tensile elongation, and flexural modulus to produce desired flexibility, stiffness, and softness. For engineering thermoplastics, tensile strength is, for example, about 2000–12,000,000 psi, tensile elongation is about 2–1500%, e.g., 50–1000%, and flexural modulus is about 2–500,000 psi.

The properties of some engineering thermoplastics are given in the table below (see Modern Plastics Mid-October Encyclopedia Issue 1990):

| MATERIAL | TENSILE STRENGTH (PSI × 1000) (ASTM D638) | TENSILE ELONGATION (%) (ASTM D638) | FLEXURAL MODULUS (psi × 1000) (ASTM D790) |
| --- | --- | --- | --- |
| PMMA | 7–10,000 | 2.0–10 | 325–460 |
| Nylon-6* | 6,500 | 65 | 250 |
| Nylon-6/6* | 7,000 | 125 | 240 |
| Nylon-11* | 8,000 | 300 | 150 |
| Nylon-12* | 5–9,000 | 250–350 | 27–190 |
| PEBAX Type* | 2–7,000 | 350–680 | 3.0–65 |
| Polycarbonate | 9,500 | 110 | 345 |
| PBT | 8,200 | 50–300 | 330–400 |
| PET | 7–10,500 | 30–300 | 350–450 |
| HDPE* | 3–4,500 | 10–1200 | 145–225 |
| Polypropylene | 4–6,000 | 100–600 | 170–250 |
| Polystyrene | 5–7,500 | 1.2–2.5 | 380–490 |
| PVDC* | 3–5,000 | 160–240 | 55–95 |

*= Can be crosslinked via irradiation (e-Beam or gamma)

The polymers may be compounded with radiopaque particles, such as bismuth subcarbonate (e.g., 30% by weight) or tungsten (e.g., 80% by weight), prior to processing. The polymer may include reinforcing elements, such as metal wires or Kevlar fibers, that are oriented along with the polymer. However, a particular advantage of implements and methods described herein is that reinforcing elements are not necessary for imparting good torque transmission properties for most applications because of the orientation of the structural polymer.

For helical orientation, the polymer is typically heated to temperatures above the glass transition temperature but well below the melting point. For example, temperatures may be in the range of about 200–250° F. In embodiments, multiple heat treatments can be used. For example, the polymer may be oriented in a first heat treatment at a relatively low temperature of around 200° F., as described above. In a second, subsequent heat treatment at a higher temperature, for example, about 300° F., the oriented polymer member is heated under tension but without rotation or stretching to heat set the polymer to improve its dimensional stability.

This can be achieved by running the oriented member back over the heater without rotation and only slight tension to prevent shrinking. Alternatively, heat setting can be performed in a separate oven equipped with a holders to maintain tension. Helical orientation and heat set may be effected in a single operation for many polymers at a temperature of around 250° F. The temperature can be programmed to vary during the course of processing. This feature may be useful when forming a device that has different polymers along its length.

The rotation and translation speeds can be varied to affect the torque fidelity. This varies the pitch length of the helical paths. In embodiments, the pitch length, PL, is at least about 1.5, e.g., two to five times, the outer diameter of the oriented rod or tube. The pitch length can be approximated by drawing a line (e.g., with permanent ink) parallel to the axis of the polymer member prior to processing. After processing, the line traces a helical pattern that approximates the helical orientation of the polymer. Typical rotation rates are in the range of about 100–200 rpm. The ratio of the translation speed of the two stations is typically 2:1 to 4:1. The translation speed of each station is typically in the range of 10–100 cm/min. Very slow translation speeds are also possible. If the translation speed is excessive, the polymer will not be heated sufficiently to cause twisting and stretching. In a case with a 3:1 stretch ratio, station 42 may be translated at about 30 cm/min, while station 44 is translated at about 90 cm/min, with the stations moving apart at about 60 cm/min. Larger diameter members can be processed at slower speeds to permit sufficient heating time or a longer heating stage can be used. For larger members, active cooling apparatus can be used to quickly cool and quench the polymer.

The translation speeds can be programmed to vary stretch ratios and residence time over the heater. This feature may be particularly useful for manufacture of a device that has different polymers along its length or different orientation properties (e.g., pitch length) along its length. The translation speed can also be varied to vary the stretch ratio and thus, the diameter of the finished device. Higher stretch ratios result in smaller diameters and, typically, lower device elongation. Translation speed should be sufficient to allow the member to be heated above the glass transition temperature. The apparatus can be scaled to process many members simultaneously by providing multiple chucks and compression fittings at the holding stations and a heater of appropriate size. It is also possible to sequentially treat the member by stretching under tension while heating but without twisting in a first step, followed by twisting while heating and placing the member under tension but without stretching in a subsequent step.

After treatment, the member should be substantially straight without excessive bends or a gross helical shape. In some cases, the torque transmission of the processed element can be improved by permitting the element to relax in an unrestrained state for a period of time (e.g., 4 to 24 hours) after processing. For example, the member can be hung vertically from one end. During the relaxation period, the member may unwind several turns. Processed elements that have a pitch length in the preferred ranges and have been heat set are typically not relaxed prior to use. In addition, the oriented devices should typically be stored or packaged in a generally straight configuration rather than coiled. Likewise, the devices are kept straight during sterilization or any other heating process. In cases in which an element has been coiled in storage, it can be straightened with a wire straightener device prior to use.

Referring to FIG. 3a, torque transmission can be tested by wrapping a processed, oriented element 3 near its midportion, at a location, L, e.g., about 40 inch from the proximal end, around a rod 5 that has a diameter of about 5 inch. The proximal end is then rotated (arrow 7) and the distal end monitored to determine the amount of rotation a and to monitor whipping. Under these conditions, polymer elements treated as discussed herein can exhibit 1:1 torque transmission without substantial whipping. However, this test represents an extreme condition for many applications. Torque transmission can be improved by the techniques discussed above to levels sufficient for particular uses without achieving 1:1 transmission in this test.

The inventions will be further described by way of the following embodiment examples.

EXAMPLE 1

Referring to FIG. 4, in an embodiment, a high torque fidelity, variable stiffness guidewire 70 is formed entirely of a single polymeric material, PET. The guidewire has been helically oriented as indicated by segment line 75. The guidewire 70 has an overall length $L_1$, about 60 inch. It includes a proximal portion 71 with a length $L_2$, of about 54 inch and a diameter $d_1$, about 0.035 inch, a tapering transition portion 72 with a length $L_3$, about 3 inch, and a highly flexible distal portion 73 with a length $L_4$, about 3 inch, and a diameter $d_2$, about 0.005 inch. The guidewire terminates in an atraumatic ball 77 that prevents vessel puncture.

Referring to FIG. 4a, the wire 70 can be formed from a polymer member 70' having an overall length $L_1'$, about 20 inch, a proximal portion 71' with a length $L_2'$, about 18 inch, and a diameter $d_1'$ about 0.060 inch, a transition portion 72' extending a length $L_3'$, about 1 inch, and a distal portion 73' extending over a length $L_4'$, about 1 inch, and having a diameter $d_2'$, about 0.009 inch. The member 70' can be formed by extrusion or molding by techniques well-known in the art.

The member 70' can be processed using the techniques discussed above with respect to FIG. 3 to form the guidewire 70. For example, the draw ratio between station 42 and station 44 is about 3:1, with the ends of polymer member 70' moving apart at about 60 cm/min. The rotation rate at station 42 is about 170 rpm. The member is heated to about 250° F. After the distal portion 73' has been treated, the translation, rotation, and heating are interrupted so that compression fittings 63, 65 can be positioned along the arm 43 and clamped to the flexible distal section to reduce stress while the remainder of the member is processed. Rotation, translation, and heating are then resumed to process the rest of the member to form wire 70.

EXAMPLE 2

Figure 5:
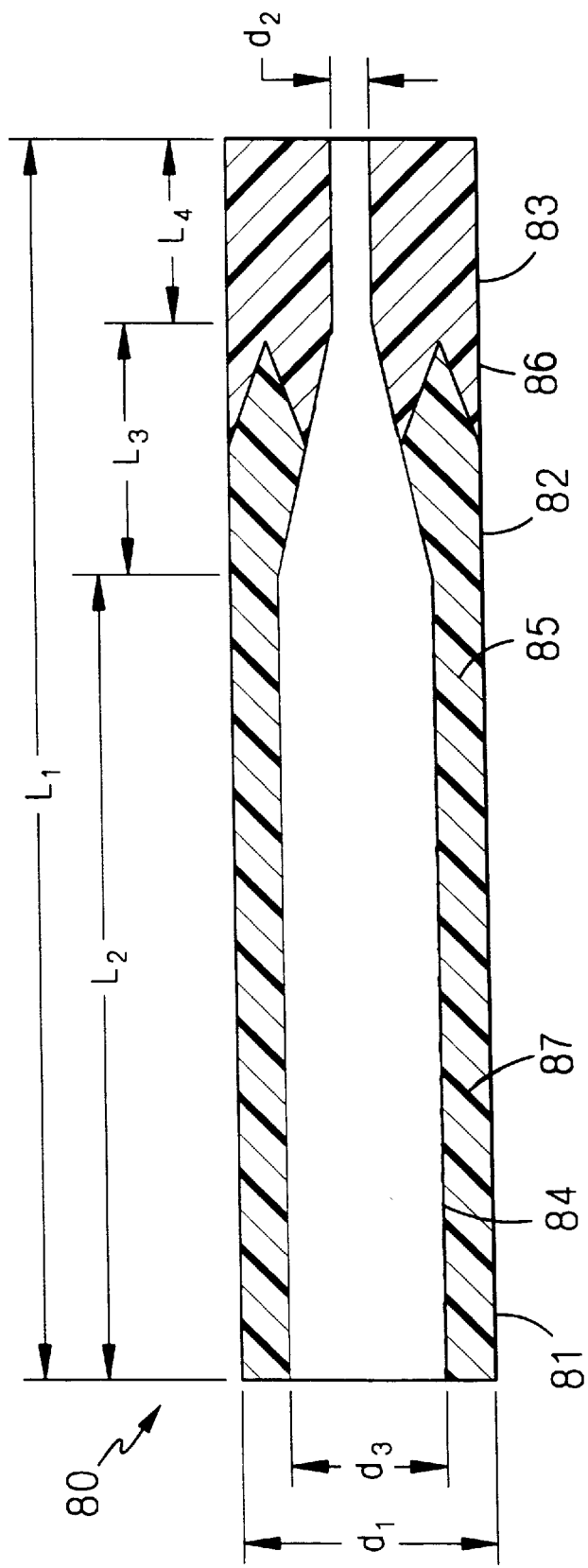

Referring to FIG. 5, in an embodiment, a high torque fidelity, variable stiffness guidewire 80 is formed entirely of polymers and includes three different polymers. The guidewire 80 includes a proximal portion having a length $L_1$, about 5 feet and a diameter $d_1$, about 0.035 inch, a transition portion 82, of length $L_3$, about 3 inch, and a distal portion 83 having a length $L_4$, about 1 inch. The guidewire is formed with an inner core 84 of relatively stiff PET (intrinsic viscosity 0.75, available as Clear Tuf 8006 from Shell Corp.) extending the full length of the guidewire and having a diameter $d_3$, about 0.030 inch, in the proximal portion, a taper in the transition portion, and a diameter $d_2$, about 0.005 inch, in the distal portion. The guidewire also includes an outer jacket 85 of a relatively fibrillation resistant nylon (nylon-12, L-1700 or L-2101, natural (clear), available from Hüls America, Inc.) that has a thickness of about 0.0025 inch in the proximal portion and extends from the proximal portion through the transition region. The guidewire further includes a soft outer layer of PEBAX (PEBAX 3533, clear, available from Atochem, France) in the transition and distal portions. The polymer element has been helically oriented as indicated by line segment 87.

Figure 5A:
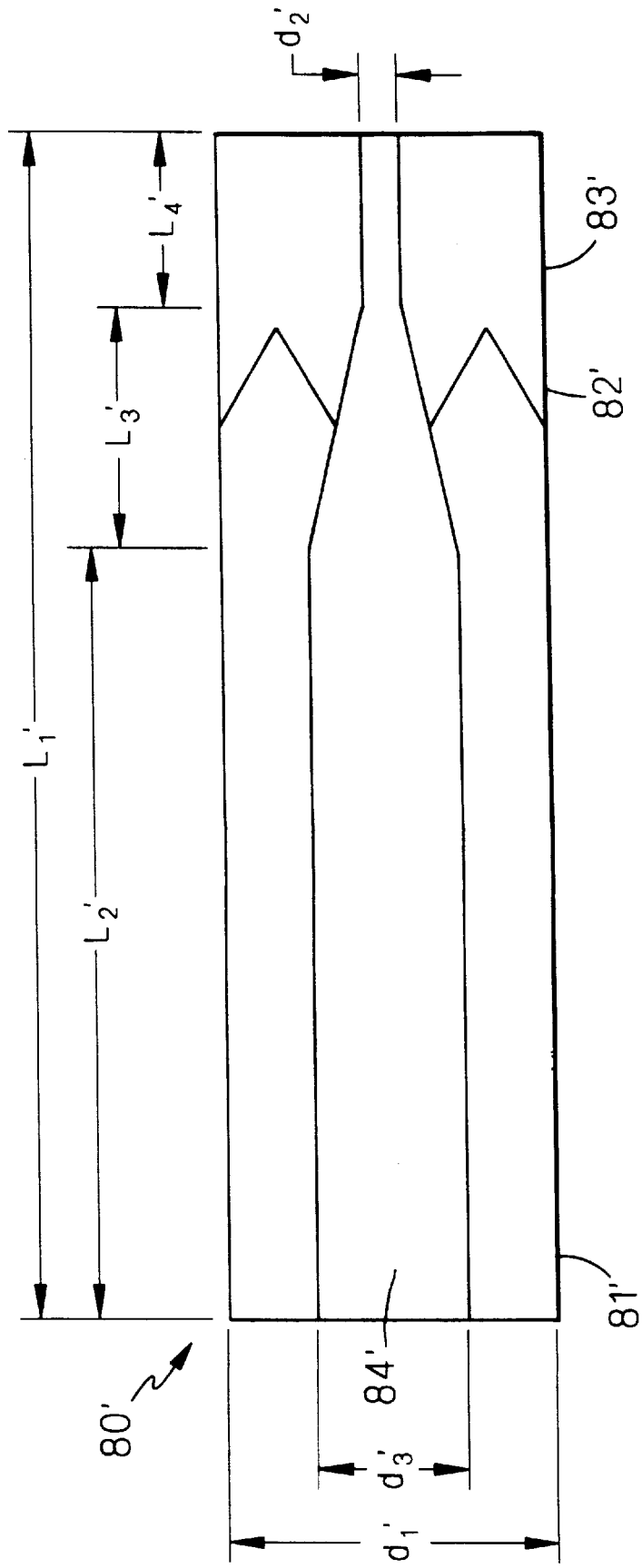
FIG. 5a is a similar view of a polymer member which is processed to form the guidewire.

Referring to FIG. 5a, the guidewire 80 can be formed from a polymer member 80' having an overall length $L_1'$, about 2.5 feet, and an outer diameter of $d_1'$, about 0.065 inch. The member 80' has a proximal portion 81' having a length of about $L_2'$ about 2.1 inch, a transition portion of length $L_3'$, about 1 inch, and a distal portion 83' having a length $L_4'$, about 2 inch. The member 80' includes a stiff core 84' of PET with a diameter $d_3'$, about 0.052 inch in the proximal portions and a diameter $d_2'$, about 0.009 inch in the distal portions. The member 80 also includes nylon outer jacket 85 and PEBAX jacket 86. Member 80' can be coextruded according to methods described in Wang, U.S. Ser. Nos. 08/230,333 and 08/230,310, incorporated infra.

The member 80' can be processed to form guidewire 80 using the techniques discussed above with respect to FIG. 3. The draw ratio between station 42 and station 44 is about 3:1 with the stations moving apart at about 50 cm/min. The rotation rate at station 42 is about 150 rpm. The member is heated to about 200° F. during processing. After the distal portions, including the PEBAX, have been processed, the translation, rotation, and heating are interrupted so that compression fitting 63, 65 can be positioned along the arm 44 to hold the distal 10 cm of the member and reduce stress in this flexible, soft section while the remainder of the member is processed. Rotation, translation, and heating is then resumed to treat the rest of the member. After this treatment, the member is heat set without rotation at about 300° F. It is believed in this final heating step, PET and nylon are heat set in the helically oriented configuration, while the PEBAX relaxes somewhat from the helical orientation. Alternatively, the distal end, including the PEBAX, is heat set at a lower temperature, e.g., 220° F. to avoid any heat-induced retention.

EXAMPLE 3

Figure 6:
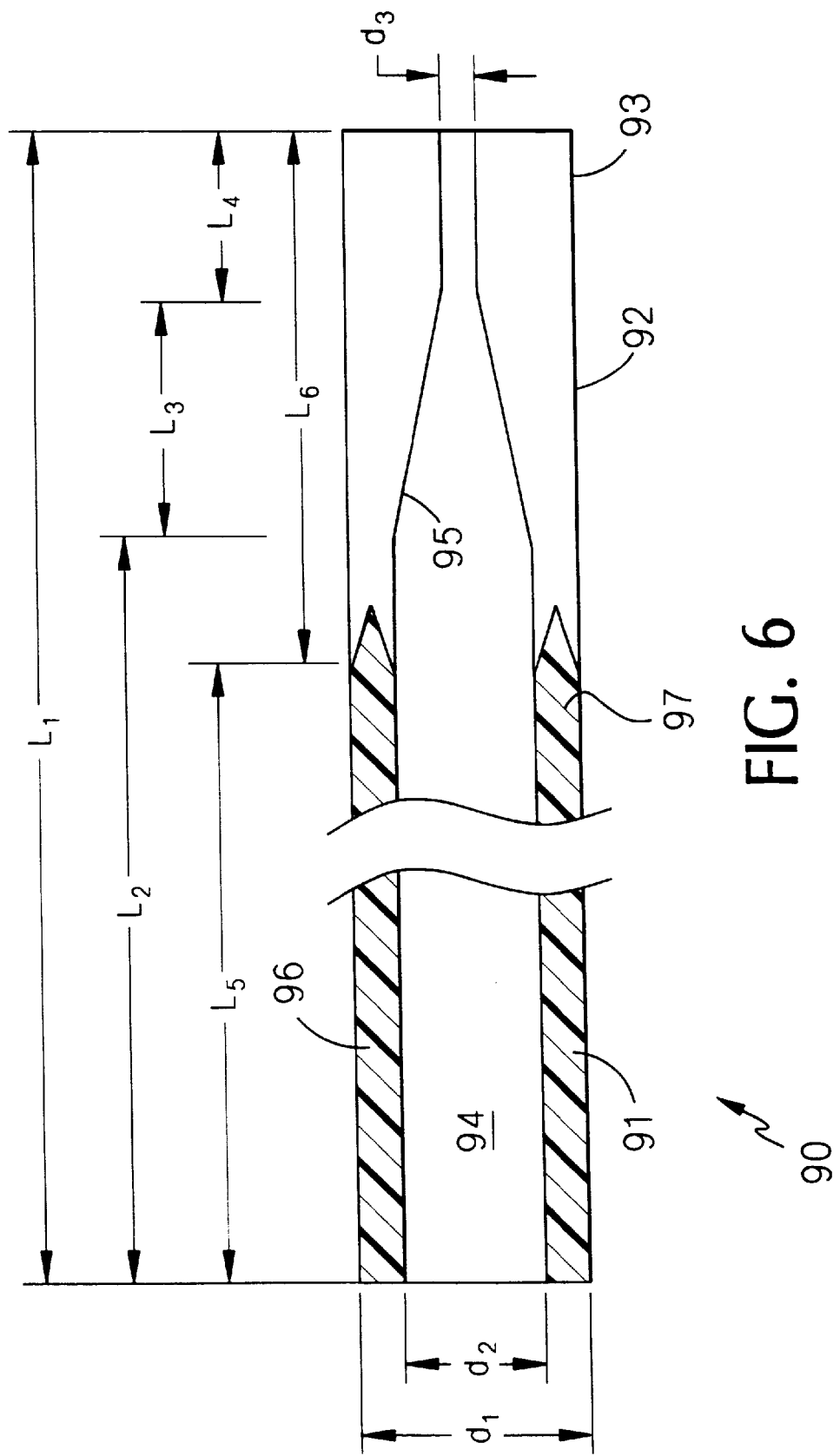
FIG. 6 is a cross-sectional side view of a guidewire as discussed in Example 3.

Referring to FIG. 6, a high torque fidelity, variable stiffness guidewire 90 includes a variable stiffness polymer jacket 96 and a metal core 94. The wire 90 has an overall length $L_1$, about 60 inch, and includes a proximal portion 91 having a length $L_2$, about 52 inch, and a diameter $d_1$, about 0.018 inch, a transition section 92 having a length $L_3$, about 6 inch, and a distal portion 93 having a length $L_4$, about 2 inch. The inner core 94 is nitinol and has a diameter $d_2$, about 0.014 inch, in proximal portions, a taper 95 in the transition region and a diameter $d_3$, about 0.002 inch, in distal portions. The outer jacket 96 has variable stiffness. In the proximal portion, the jacket includes relatively stiff PEBAX (PEBAX 7033, available from Atochem), extending $L_5$, about 51 inch and in the distal portion the jacket includes soft PEBAX (PEBAX 3533, available from Atochem), extending $L_6$, about 9 inch. The polymer element has been helically oriented as indicated by segment line 97.

Figure 7:
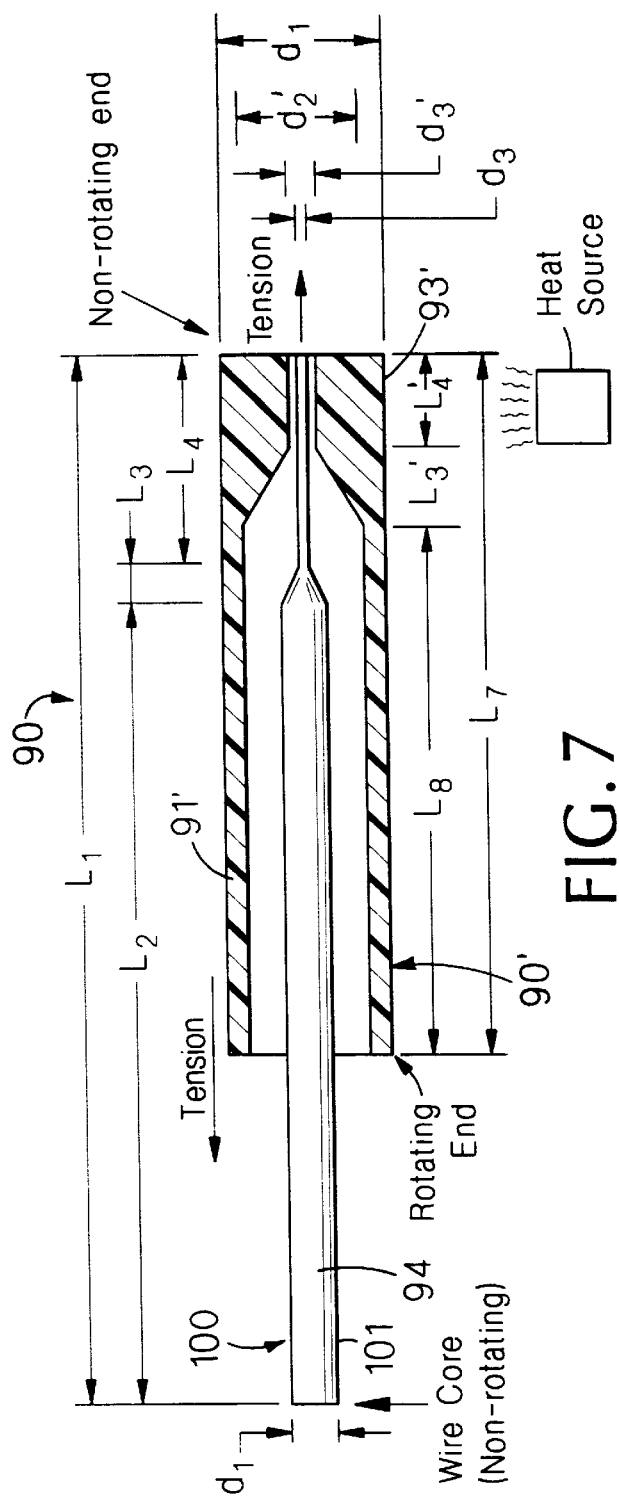
FIGS. 7 and 7a are schematics illustrating manufacture of the guidewire in FIG. 6.
Figure 7A:
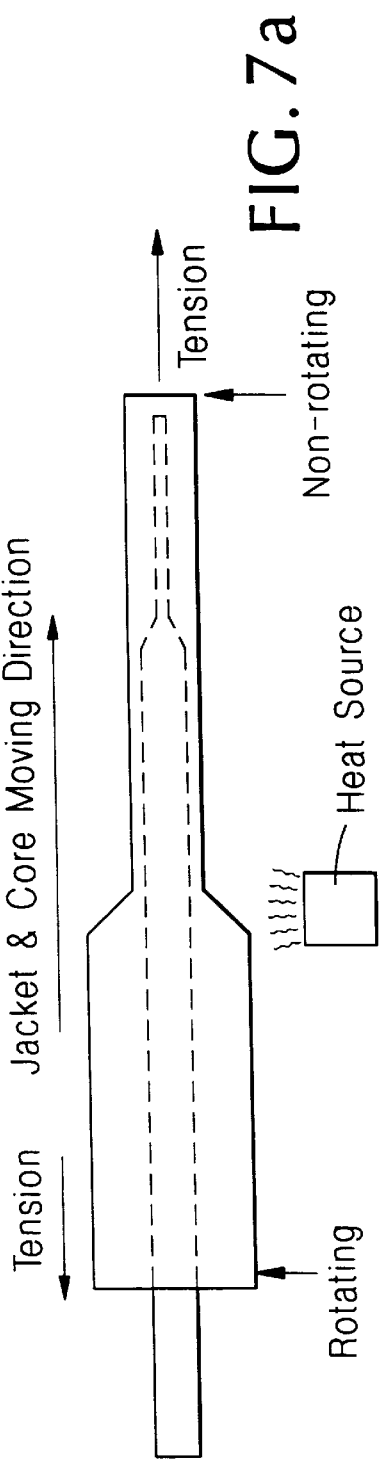

Referring to FIGS. 7 and 7a, the guidewire 90 is formed from a polymer member 90' and a nitinol core 100. The nitinol core has an overall length that is the same as the guidewire core, that is, $L_1$, about 60 inch, a proximal portion 101 having an outer diameter $d_1$, about 0.014 inch, and a length $L_2$, about 51 inch, a transition portion 102 having a length $L_3$, about 6 inch, and a distal portion having a length $L_4$, about 3 inch, and a diameter $d_3$, about 0.002 inch. The core 94 is positioned within the polymer member 90'. Polymer member 90' has an overall length $L_7$, about 20 inch, and a diameter $d_1'$, about 0.032 inch. The member 90' includes a proximal portion 91' having a length $L_8$, about 17 inch, and an inner lumen diameter $d_2'$, about 0.024 inch, a transition portion $L_3'$, about 2 inch, and a distal portion 93' having a length $L_4'$, about 1 inch, and an inner diameter $d_3'$, about 0.0035 inch. The stiffer PEBAX extends proximally about 17 inch from the proximal end. The softer PEBAX extends to the distal end of the member. The member 90' can be coextruded by techniques described in U.S. Ser. Nos. 08/230,333 and 08/230,310, incorporated infra. The variation in inner lumen diameter and outer diameter along the length can be effected by controlling air pressure and line speed of the tubing puller. Lower air pressures produce smaller inner diameters. Slower speeds produce thicker walls.

The wire 90 can be formed from the member 90' and nitinol core 94 by techniques discussed above with respect to FIG. 3. The distal portion 93' of the member 90' is positioned at station 44 and clamped such that the member and the core are held together. The proximal portion 91' of member 90' is clamped a station 42 to hold the member 90' so that it can be rotated and translated. However, the proximal portions 101 of the core extend through the member and through the station chuck so that the member 90' and core are not clamped together.

Referring to FIG. 7a, during processing, the member 90' is placed under tension and rotated relative to the core while heating. The polymer member 90' shrinks over the core 94 to form a unitary composite guidewire 90. The draw-ratio between station 42 and station 44 is about 3:1, with the ends moving apart at about 60 cm/min. The rotation rate is about 200 rpm. The member is heated to about 200° F.

In use, the hard plastic of the proximal end of the wire improves resistance to cutting by the beveled end of entry needles and offers good abrasion resistance. The jacket can be made thin at the proximal end which allows a larger diameter core for the same diameter wire. The stiff jacket also increases stiffness of the wire at the proximal end. The soft PEBAX of the distal end enhances flexibility and atraumatic advance. In other embodiments, with a thermoplastic polymer or a plastically degradable metal in the core at the distal end, the guidewire may be tip-formed by heating and bending prior to delivery into the body. In other embodiments, the core is a nonmetal filament, such as glass or Kevlar.

EXAMPLE 4

Figure 8:
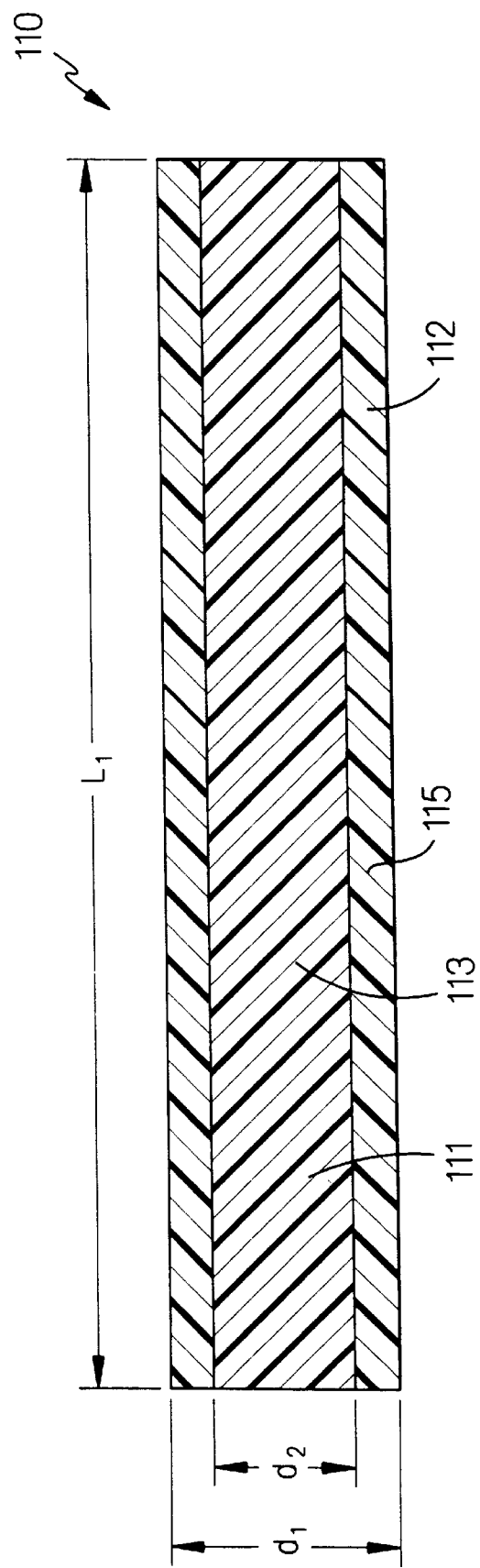
FIG. 8 is a cross-sectional side view of a guidewire as described in Example 4.

Referring to FIG. 8, in another embodiment, a guidewire 110 is formed of an inner polymer core 111 that has been helically oriented in one direction, as indicated by segment line 113, and an outer polymer jacket 112 that has been helically oriented in the opposite direction, as indicated by segment line 115. The guidewire has an overall length $L_1$, about 60 inch, and a diameter $d_1$, about 0.035 inch. The core ill has a diameter $d_2$, about 0.025 inch. The jacket 112 has a thickness of about 0.005 inch. The jacket is formed of relatively stiff PEBAX (available as PEBAX 7033 from Atochem) and the core is formed of a stiff PEBAX (available as PEBAX 6033 from Atochem). The guidewire also exhibits resistance to cutting or tear propagation in any direction, and resistance to breakage or kinking.

Figure 9:
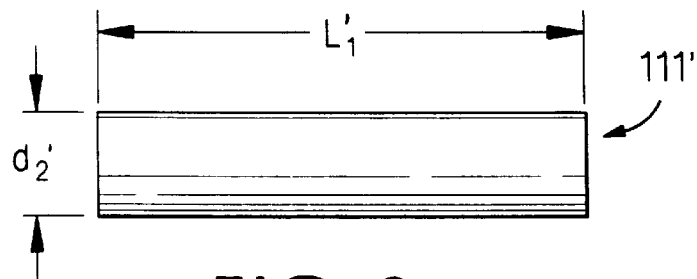
FIGS. 9 to 9b are schematics illustrating the manufacture of the guidewire in FIG. 8.
Figure 9A:
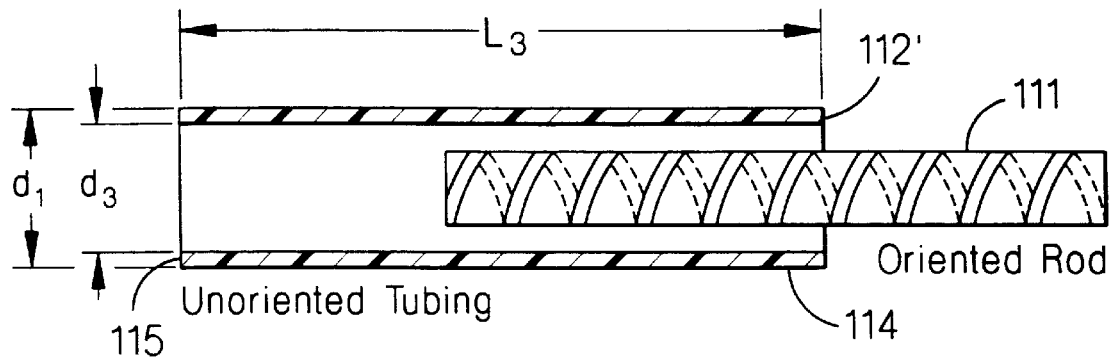

Referring to FIGS. 9 and 9a, the guidewire 110 is formed from a core member 111' having an overall length $L_1'$, about 20 inch, and a diameter $d_2'$, about 0.045 inch. The member 111' is oriented as discussed above with respect to FIG. 3. In this example, the draw-ratio between stations 42 and 44 is about 3:1 with the stations moving apart at about 50 cm/min. The rotation rate at station 42 is about 150 rpm. The member 111' is heated to about 250° F. After this treatment the core 111 is placed within a tubular member 112' that has a length $L_3$, about 20 inch, an outer diameter $d_1$, about 0.060 inch, and an inner lumen diameter $d_3$, about 0.040 inch.

Figure 9B:
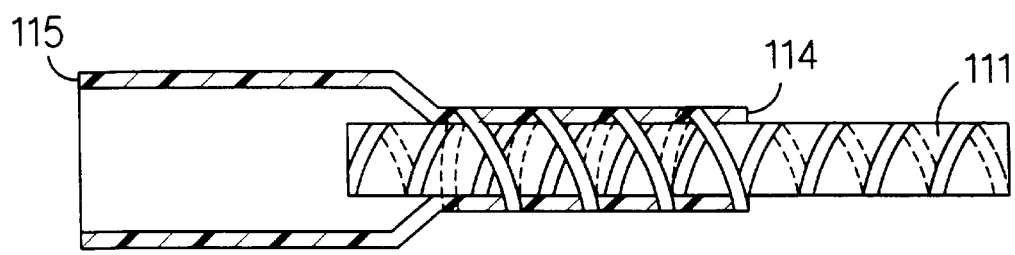

Referring to FIG. 9b, the member 111 and 112' are processed using techniques discussed above with respect to FIG. 3 and Example 3. An end 114 of member 112' is clamped at station 44 and the other end 115 is clamped at station 42, The ends are clamped in a manner that rotates and places the member 112' under tension at end 115 without placing the member 111 under tension or torque. As member 112' is rotated under tension while heating, its inner diameter shrinks to correspond to the outer diameter of member 111. The rotation at end 115 is in a direction that is opposite the rotation used during processing of member 111'. In this manner, the inner core 111 is processed to orient the polymer in one helical direction while the member 112 has polymer orientation in the opposite helical direction.

In embodiments, the wire can be tapered or a combination of stiff and flexible polymer can be used to vary the stiffness along the length. In a particular modification of this example, rather than a guidewire, the oriented member can be dimensioned for use in other torque transmission applications, such as for example, rotary ultrasound shafts, remote drilling devices (e.g., for dentistry) and arthrectomy cutters.

EXAMPLE 5

Figure 10:
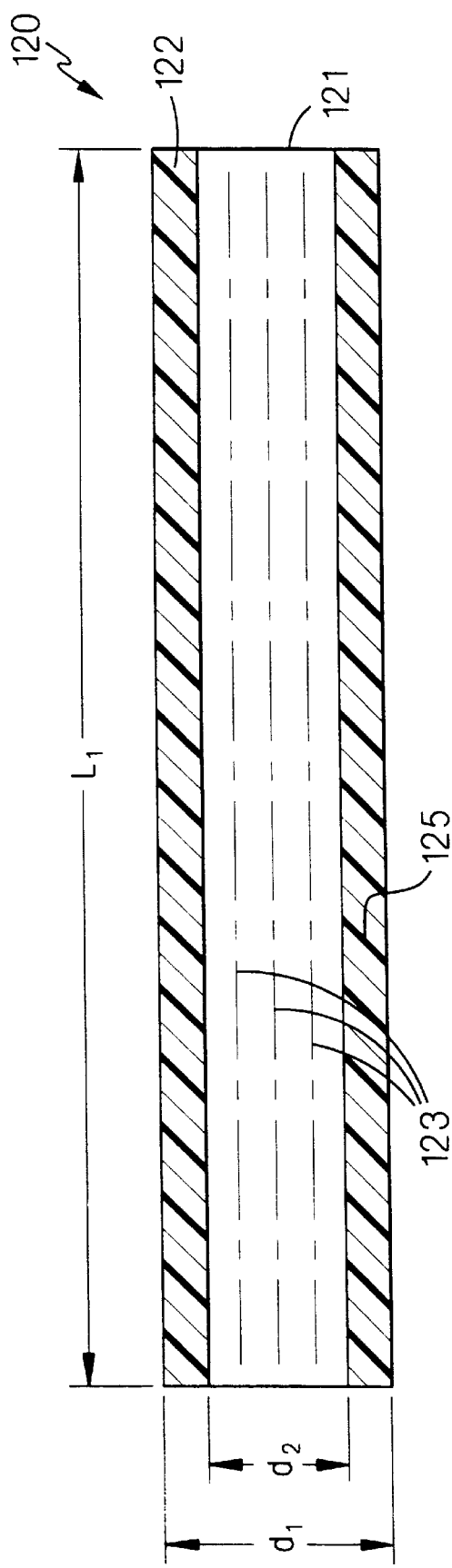
FIG. 10 is a cross-sectional side view of a guidewire as described in Example 5.

Referring to FIG. 10, in an embodiment, a high torque fidelity guidewire 120 includes an inner core 121 that has an axial orientation, as indicated by segment lines 123, and an outer jacket 122 that has a helical orientation, as indicated by segment line 125. The guidewire 120 has an overall length $L_1$, about 60 inch, and an outer diameter $d_1$, about 0.035 inch. The core 121 is formed of a relatively stiff PEBAX (available as PEBAX 7033 from Atochem) and has a diameter $d_2$, about 0.030 inch. The jacket 122 is formed of a softer PEBAX (available as PEBAX 6033 from Atochem) and has a thickness of about 0.0025 inch.

The guidewire 120 can be formed by the procedure set forth above in Example 4 with the modification that the core is axially oriented by placing it under tension in the apparatus described in FIG. 3 without rotation.

Other embodiments of this construction include catheters and drive shafts. Devices of this construction can exhibits very low, e.g., about 15% ultimate axial elongation.

EXAMPLE 6

Figure 11:
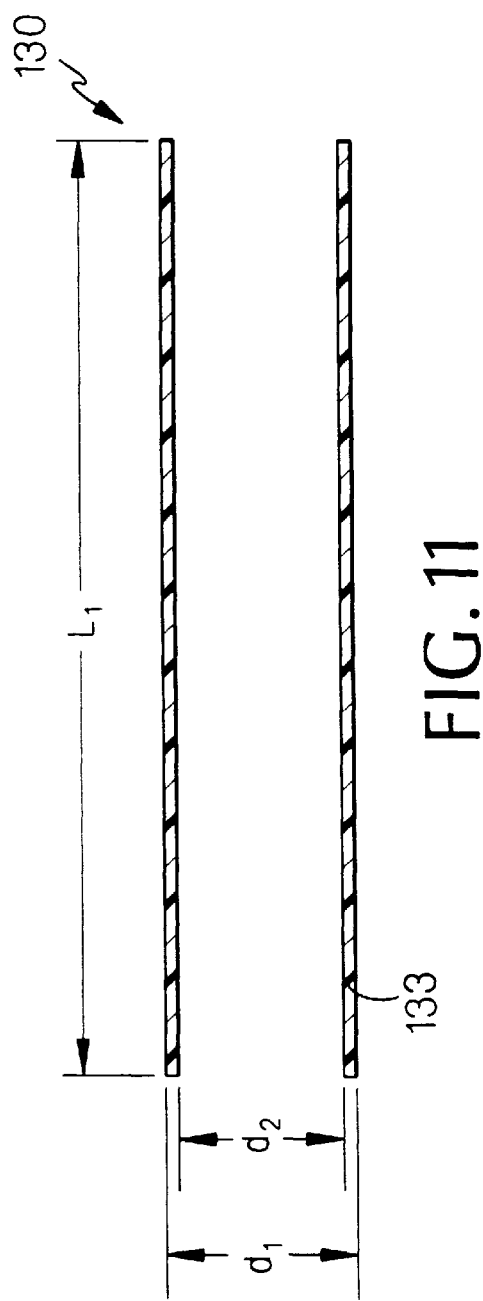

Referring to FIG. 11, in an embodiment, a high torque fidelity catheter 130 is formed of polymeric material. The catheter 130 has an overall length $L_1$, about 42 inch, an outer diameter $d_1$, about 0.078 inch, and an inner diameter $d_2$, about 0.037 inch. The polymer is PEBAX (available as PEBAX 7033 from Atochem). The polymer element has been helically oriented as indicated by segment line 133.

Figure 11A:
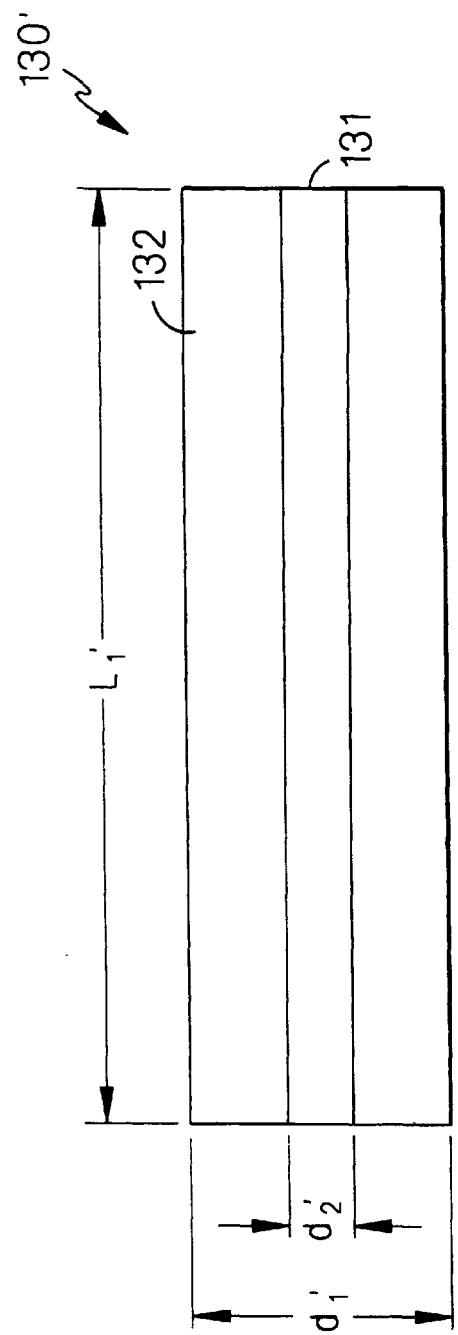
FIG. 11a is a similar view of a polymer member which is processed to form the catheter.

Referring to FIG. 11a, the catheter 130 is formed from a polymer member 130' that includes an inner core 131 of high density polyethylene and an outer jacket 132 of PEBAX. The member 130' has an overall length $L_1'$, about 14 inch, and an outer diameter $d_1'$, about 0.134 inch. The core 131 has a diameter $d_2'$, about 0.064 inch.

The member 130' is processed by techniques described above with respect to FIG. 3. The draw ratio between stations 42 and 44 is about 3:1 with the stations moving apart at about 50 cm/min. The rotation rate at station 42 is about 150 rpm. The member is heated to a temperature of 220° F. After this treatment, the member is heated subsequently without rotation at 270° F. This subsequent heating step melts the polyethylene core 131, which relaxes the helical orientation. By relaxing the helical orientation of the polyethylene, the core can be easily stretched, reducing its diameter, and allowing it to be pulled from within the jacket.

In a modification of this example, the core 131 is formed of a noncrystalline polymer, for example polystyrene, which relaxes in the subsequent heat treatment step. In embodiments, a tube may be formed with two jacket layers that are oppositely helically oriented as described in Examples 4 and 5. The tubes can exhibit improved burst strength and resistance to kinking.

EXAMPLE 7

Figure 12:
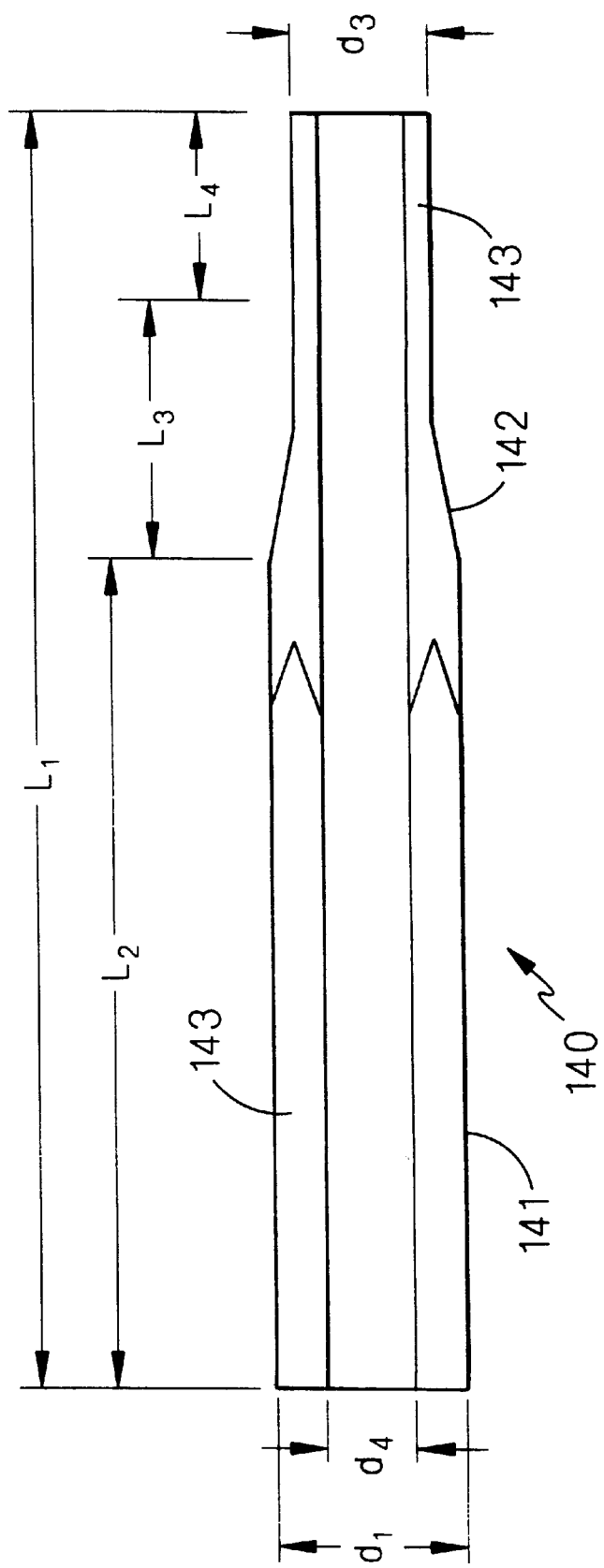
Figure 12A:
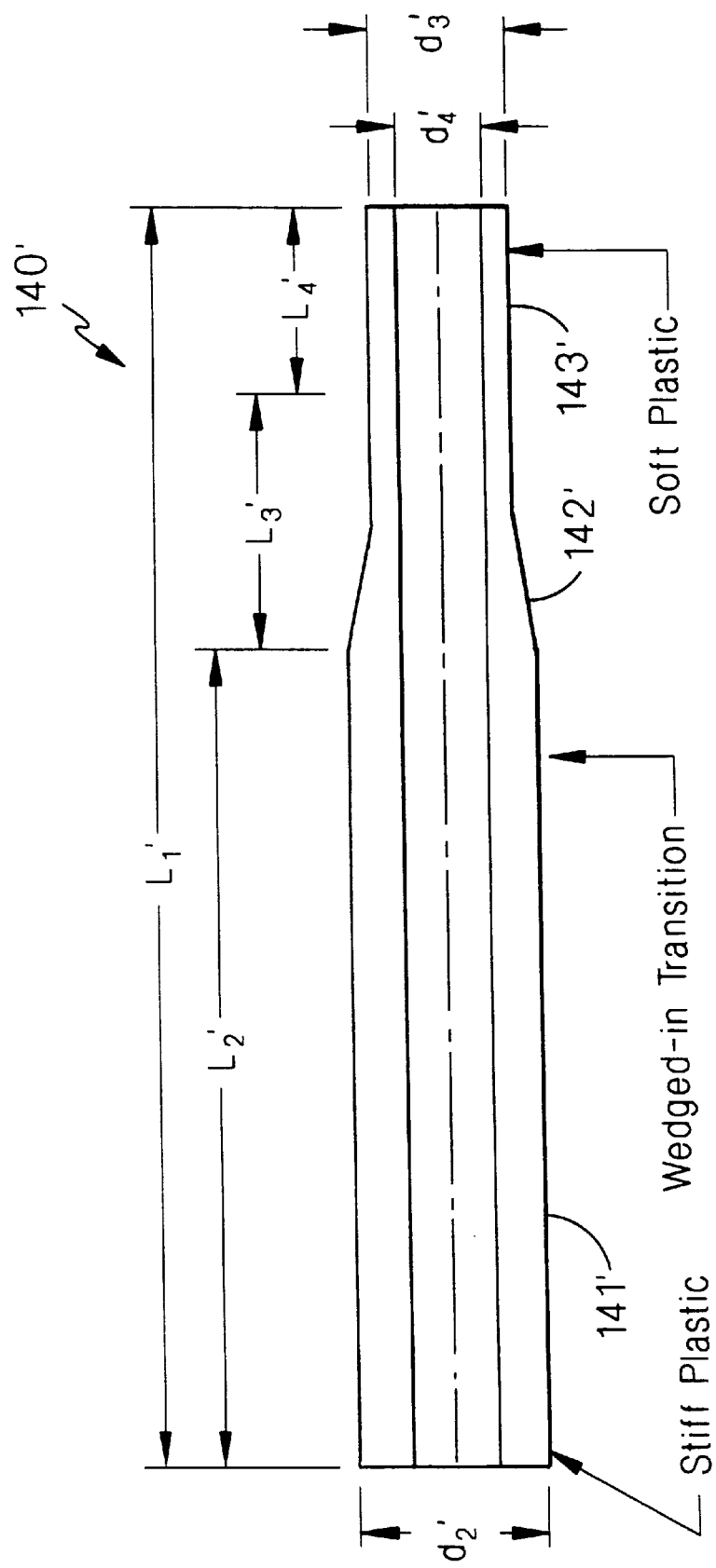
FIG. 12a is a cross-sectional side view of a polymer member which can be processed to form the catheter.

Referring to FIG. 12, in an embodiment, a high torque, variable stiffness catheter 140 is formed of multiple polymer materials. The catheter 140 has an overall length $L_1$, about 42 inch, with a proximal portion 141 having a length $L_2$, about 38 inch and a diameter $d_1$, about 0.078 inch, a transition portion 142 having a length $L_3$, about 2 inch, and a distal portion having a length $L_4$, of about 2 inch, and an outer diameter $d_3$, about 0.065 inch. The catheter 140 includes a lumen extending its length having an inner diameter $d_4$, about 0.037 inch. The proximal portion 141 is formed of a relatively stiff plastic, PEBAX, (available as PEBAX 7033 from Atochem) and the transition and distal portions are formed of a relatively soft polymer, (available as PEBAX 5033 from Atochem). The polymer element has been helically oriented as indicated by segment line 143.

Referring to FIG. 12, the catheter 140 is formed from a member 140' that has an overall length $L_1'$, about 14 inch. The member 140' has a proximal portion 141' with a length $L_2'$, about 12.6 inch, and an outer diameter $d_2'$ about 0.134 inch, a transition section 142' having a length $L_3'$, about 0.7 inch, and a distal portion 143' having a length $L_4'$, about 0.7 inch, and an outer diameter $d_3'$, about 0.112 inch. The member 140' has a lumen having a diameter $d_4'$, about 0.064 inch. The member 140' includes a relatively stiff polymer, PEBAX, (available as PEBAX 7033 from Atochem) in the proximal portion and a relatively soft polymer, (available as PEBAX 5033 from Atochem). The member 140' can be coextruded according to the methods discussed in the Wang U.S. Ser. Nos. 08/230,333 and 08/230,310 incorporated infra.

The member 140' is processed according to the technique discussed above with respect to FIG. 3. The draw-ratio between stations 42 and 44 is about 3:1, with the stations moving apart at about 50 cm/min. The rotation rate is about 150 rpm. The member is heated to about 200° F.

EXAMPLE 8

Referring to FIG. 13, in an embodiment, a high-torque fidelity guidewire 150 includes a proximal portion 152 and a distal portion 154. The proximal portion 152 includes a metal core 156, for example, stainless steel or nitinol, surrounded by a polymer jacket 158, for example, PTFE. The jacket 158 may or may not be helically oriented. The core preferably provides mechanical characteristics sufficient to transmit torque with high fidelity along the length of the proximal portion 152. The metal core 156 extends a short distance into the distal portion 154 of the wire. The distal portion 154 is made of a helically oriented polymer body 160 that includes a first polymer portion 161, e.g., PEBAX 7033, coextruded with a second, more flexible, polymer portion 103, e.g., PEBAX 3533, which extends to a distal tip 162.

The guidewire 150 has an overall length L1, of about 150 cm. The distal portion 154 has a length L2, of about 40–60 cm. The core wire 156 extends a length L3, about 3–5 cm into the distal portion 154. The outer diameter of the guidewire 150 is about 0.030 inch. The core 156 has a diameter of about 0.023 inch for most of its length and tapers distally in the distal region over a length of about 6 inch to about 0.004 inch diameter. The taper begins at a point just proximal of the distal portion 160.

The guidewire 150 can be formed by procedures set forth above. In a particular example, the core 156 is coated with polymer to form the jacket 158 over most of its ratio between stations 42 and 44 is about 3:1, with the stations moving apart at about 50 cm/min. The rotation rate is about 150 rpm. The member is heated to about 200° F.

EXAMPLE 8

Referring to FIG. 13, in an embodiment, a high-torque fidelity guidewire 150 includes a proximal portion 152 and a distal portion 154. The proximal portion 152 includes a metal core 156, for example, stainless steel or nitinol, surrounded by a polymer jacket 158, for example, PTFE. The jacket 158 may or may not be helically oriented. The core preferably provides mechanical characteristics sufficient to transmit torque with high fidelity along the length of the proximal portion 152. The metal core 156 extends a short distance into the distal portion 154 of the wire. The distal portion 154 is made of a helically oriented polymer body 160 that includes a first polymer portion 161, e.g., PEBAX 7033, coextruded with a second, more flexible, polymer portion 103, e.g., PEBAX 3533, which extends to a distal tip 162.

The guidewire 150 has an overall length L1, of about 150 cm. The distal portion 154 has a length L2, of about 40–60 cm. The core wire 156 extends a length L3, about 3–5 cm into the distal portion 154. The outer diameter of the guidewire 150 is about 0.030 inch. The core 156 has a diameter of about 0.023 inch for most of its length and tapers distally in the distal region over a length of about 6 inch to about 0.004 inch diameter. The taper begins at a point just proximal of the distal portion 160.

The guidewire 150 can be formed by procedures set forth above. In a particular example, the core 156 is coated with polymer to form the jacket 158 over most of its length, while leaving a distal length of the core exposed. The distal portion 154 is formed by placing a tube-form polymer member under tension while applying rotational motion to helically orient the polymer as described, e.g., with respect to Example 7 above. The tube-form member has a length of about one-third and a diameter of about two times, the dimensions of the final oriented body. The first polymer is about two-thirds the length and the second polymer about one-third the length of the member. The member is extruded with an inner lumen having a diameter of about 0.002–0.008" at the distal end and about 0.025" at the proximal end. The member can be oriented with a draw rate of about 3:1, speed of about 50 cm/min, rotation rate of about 150 rpm and temperature of about 200° F. A tapered mandrel having a diameter corresponding to the diameter of the end of the core 156 may be provided in the end of the tube-form such that the inner lumen of the distal portion will have a diameter substantially corresponding to the core after orientation. The lumen 164 in the distal portion can be open, as illustrated. Alternatively, the lumen can be closed near the distal tip 162, for example, during orientation or by heating and melting the distal tip after orientation. The oriented body may also be drawn to form a tapered profile. The wire 150 is assembled by inserting the core 156 extending from the end of the proximal portion 152 into the lumen 164 and gluing the portions together using an adhesive, e.g., a cyanoacrylate or U.V. curable. Any mismatch in the outer diameter of the proximal and distal portions can be smoothed by a thin layer of polymer. The wire 150 can be provided in a package in which the proximal portion 152 is coiled to a convenient size, e.g., 9–12 inch, while the distal portion 154 is maintained in a generally straight configuration to assure that the portion 154 does not take a set.

Referring to FIG. 13a, a particular application of the wire 150 is to assist in delivery and operation of a sphinctertome 170. The sphinctertome 170 includes a catheter body 172 with a lumen 174 and a cutting wire 176. The cutting wire 176 extends through the lumen 174 for most of its length, but near the distal end of the catheter, extends through an opening 179 in the catheter wall and is fixed at a point 178 near the distal end of the catheter. In a tensioned condition, the wire bows the distal portion of the catheter 172 in a manner that the wire is exposed and can be used for resection. The wire 176 is connected at its proximal end extending outside the body to an RF generator (not shown).

The sphinctertome 170 can be delivered over guidewire 150 to a desired treatment site. The distal portion 154 of the guidewire has a length that is selected such that the portions of the wire that are in the region of the exposed cutting wire 176 are all plastic. Typically, the wire is located in the sphinctertome such that the distal end extends about 3 inch proximally of the opening 179. When the RF energy is applied to the wire 176, the wire is not heated. The distal portion 154 being made substantially of polymer, thus permits the cutting operation to be conducted while the wire extends from the distal end of the sphinctertome which can facilitate resection by guiding or stabilizing the sphinctertome. In addition, the high-torque transmission characteristics of the wire assist in initial placement of the sphinctertome.

OTHER EMBODIMENTS

Polymer torque transmission elements can be constructed for use in many applications. For example, tubes can be sized and constructed for use as guiding catheters, microcatheters (e.g., for neurovascular applications), angiographic catheters, balloon catheter shafts, and balloons. Catheters can be constructed for use in the nonvascular physiology, e.g., the urinary tract, or G.I. tract. Rod-forms can be used as guidewires, as discussed, and in other applications where torque must be applied and transmitted along extended lengths. The torque transmission polymer devices may have particular advantages in applications where metal components would interfere with the procedure. Examples include MRI procedures, and procedures in which RF current is applied. Sphinctertomes, for example, might be delivered without the requirement that the guidewire be retracted prior to application of RF energy. Other devices such as ablation devices, e.g. heated balloons, may also be improved by the use of nonmetallic, torque transmission components. In certain MRI apparatus, such as those with C-shaped magnets, a physician can approach the patient to perform a procedure during imaging. The all-polymer high torque transmission medical devices, e.g. catheters and guidewires, could be used without interference with the MRI to perform a procedure, such as a noninvasive procedure, such as catheterization. Other applications for torque transmission members include rotatable drive shafts for acoustic imaging catheters and guidewires. In a particular example, shaft device is formed as a rod of PET polymer that is processed as discussed. Acoustic imaging catheters and guidewires are discussed in U.S. Pat. No. 5,368,035, the entire contents of which is incorporated herein by reference. Other applications are in nonmedical fields where torque transmission is required. Examples include drive shafts for automobiles, boats, power tools, and elongated fluid conduits.

In manufacture, the ends of the polymer member can be translated at different speeds in different directions. One end could be translated while the other is held stationary. The heater could also be translated. The grip members can also be programmed to grip and release the member at select locations along its length during orienting.

In manufacture of helically oriented materials with inner lumens, such as catheters, the lumen can be maintained during orientation using a teflon-coated metal rod as a mandrel (for example, instead of a polymer mandrel as described in Example 6 above). In this case, a polymer tube is oriented about the mandrel as described in Example 3. The mandrel is then pulled from the oriented member. Since the teflon coating on the exterior of the mandrel has a higher affinity for the oriented polymer than the metal rod, the metal rod can be removed leaving an oriented polymer member with a lumen including a thin coating of teflon on the lumen walls. The teflon coating on the interior of the lumen is advantageous since it can facilitate introduction of, e.g., a guidewire. In a particular example, the mandrel may be a copper rod with a thin plated silver coating. The teflon is coated over the silver at about 0.0004 inch thickness. The exposed exterior of the teflon coating is etched to enhance its ability to bond to the oriented polymer. Etching can be carried out with Teflon etchants (e.g., of the type used in the cookware industry; etching available from, e.g., HV Technologies, GA). The overall diameter of the mandrel may be, e.g., about 0.024 inch. The teflon-coated rod mandrel makes removal of the mandrel easier, particularly for oriented members of extended length, e.g., 50 or 100 cm or more. In addition, as described above, the technique provides a low friction coating on the interior of the lumen of the oriented member.

Still further embodiments are within the following claims.

What is claimed is:

1. An elongated medical instrument formed at least in part of an extended element, said element being a structural body that is composed of polymer and which is the product of the process comprising:
   providing an elongated polymer member,
   heating said polymer member above its glass transition temperature but below its melting temperature,
   simultaneously twisting and tensioning said member, and
   cooling said member to set the effect of said twisting and tensioning into said member,
   wherein said member is a part of the medical instrument.

2. The instrument of claim 1 comprising stretching said member by said tensioning.

3. The instrument of claim 2 comprising placing said polymer member in tension and rotating one end of said polymer member while holding the other end rotationally stationary.

4. The instrument of claim 2 wherein said process includes simultaneously heating, twisting, and stretching.

5. The instrument of claim 3 wherein said process includes providing a member having differential stiffness along its length.

6. The instrument of claim 1, wherein the cooled member is substantially straight.

7. The instrument of claim 1, further comprising heating the polymer member under sufficient tension to prevent the member from shrinking.

8. The instrument of claim 1, wherein the polymer member comprises a plurality of polymers along its length.

9. The instrument of claim 1, wherein tensioning the member comprises translating ends of the polymer member at different speeds.

10. The instrument of claim 1, wherein the polymer member comprises
    a core comprising a first material, and
    an outer portion comprising a second material different than the first material.

11. The instrument of claim 10, wherein the first material comprises a metal.

12. The instrument of claim 10, wherein the outer portion has differential stiffness along its length.

13. The instrument of claim 1, further comprising:
    positioning the cooled polymer member into a tubular member,
    heating the tubular member, and
    twisting the tubular member in a direction different than a twisting direction of the polymer member.

14. The instrument of claim 1, wherein the polymer member defines a lumen.

15. The instrument of claim 14, further comprising positioning an inner core in the lumen.

16. The instrument of claim 15, wherein the inner core is oriented in a direction different than a twisting direction of the polymer member.

17. The instrument of claim 15, wherein the inner core is axially oriented.

18. The instrument of claim 14, further comprising positioning the polymer member over a mandrel.

19. The instrument of claim 18, wherein the mandrel comprises a polymer coating.

20. The instrument of claim 1, capable of exhibiting substantially 1:1 torque fidelity between proximal and distal ends.

21. The instrument of claim 1, wherein the member is in the form of a solid polymer rod.

22. The instrument of claim 1, wherein the polymer comprises a semi-crystalline polymer.

23. The instrument of claim 1, in the form of a guidewire.

24. The instrument of claim 1, in the form of a catheter.

25. An elongated medical instrument formed at least in part of an extended element, said element being a structural body that is composed of polymer and which is the product of the process comprising:
    heating an elongated polymer member above its glass transition temperature but below its melting temperature,
    tensioning the member,
    twisting the member, and
    cooling the member,
    wherein the member is a part of the medical instrument.

26. The instrument of claim 25, wherein twisting is performed after tensioning.

27. The instrument of claim 25, wherein twisting is performed under sufficient tension to prevent the member from shrinking and without stretching the member.

28. The instrument of claim 25, wherein tensioning the member comprises stretching the member.

29. The instrument of claim 25, wherein cooling sets the effect of the twisting and tensioning into the member.

30. The instrument of claim 25, wherein tensioning and twisting are performed while heating.

31. The instrument of claim 25, comprising placing said polymer member in tension and rotating one end of said polymer member while holding the other end rotationally stationary.

32. The instrument of claim 25, wherein said member has differential stiffness along its length.

33. The instrument of claim 25, wherein the cooled member is substantially straight.

34. The instrument of claim 25, further comprising heating the polymer member under sufficient tension to prevent the member from shrinking.

35. The instrument of claim 25, wherein the polymer member comprises a plurality of polymers along its length.

36. The instrument of claim 25, wherein tensioning the member comprises translating ends of the polymer member at different speeds.

37. The instrument of claim 25, wherein the polymer member comprises a core including a first material, and an outer portion including a second material different than the first material.

38. The instrument of claim 37, wherein the first material comprises a metal.

39. The instrument of claim 37, wherein the outer portion has differential stiffness along its length.

40. The instrument of claim 25, further comprising:

positioning the cooled polymer member into a tubular member, heating the tubular member, and twisting the tubular member in a direction different than a twisting direction of the polymer member.

41. The instrument of claim 25, wherein the polymer member defines a lumen.

42. The instrument of claim 41, further comprising positioning an inner core in the lumen.

43. The instrument of claim 42, wherein the inner core is oriented in a direction different than a twisting direction of the polymer member.

44. The instrument of claim 32, wherein the inner core is axially oriented.

45. The instrument of claim 31, further comprising positioning the polymer member over a mandrel.

46. The instrument of claim 45, wherein the mandrel comprises a polymer coating.

47. The instrument of claim 25, capable of exhibiting substantially 1:1 torque fidelity between proximal and distal ends.

48. The instrument of claim 25, wherein the member is in the form of a solid polymer rod.

49. The instrument of claim 25, wherein the polymer comprises a semi-crystalline polymer.

50. The instrument of claim 25, in the form of a guidewire.

51. The instrument of claim 25, in the form of a catheter.

* * * * *